(12) United States Patent
Ishida et al.

(10) Patent No.: US 7,964,382 B2
(45) Date of Patent: Jun. 21, 2011

(54) DNA ENCODING A PROTEIN HAVING D-LACTATE DEHYDROGENASE ACTIVITY AND USES THEREOF

(75) Inventors: Nobuhiro Ishida, Aichi (JP); Kenro Tokuhiro, Aichi (JP); Haruo Takahashi, Ogaki (JP); Eiji Nagamori, Aichi (JP); Masana Hirai, Seto (JP); Satoshi Saitoh, Aichi (JP); Tohru Ohnishi, Toyota (JP)

(73) Assignees: Kabushiki Kaisha Toyota Chuo Kenkyusho, Aichi-Gun, Aichi (JP); Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 0 days.

(21) Appl. No.: 12/324,804

(22) Filed: Nov. 26, 2008

(65) Prior Publication Data

US 2009/0275095 A1 Nov. 5, 2009

Related U.S. Application Data

(63) Continuation of application No. 10/557,306, filed as application No. PCT/JP2004/007317 on May 21, 2004, now abandoned.

(30) Foreign Application Priority Data

May 22, 2003 (JP) ................................ 2003-145085

(51) Int. Cl.
 C12N 9/04 (2006.01)
 C12N 1/20 (2006.01)
 C12N 15/00 (2006.01)
 C12P 7/56 (2006.01)
 C12P 21/04 (2006.01)
 C12Q 1/00 (2006.01)
 C12Q 1/68 (2006.01)
 C12Q 1/32 (2006.01)
 C07H 21/04 (2006.01)

(52) U.S. Cl. .................. 435/190; 435/4; 435/6; 435/26; 435/69.1; 435/71.1; 435/252.3; 435/320.1; 435/440; 435/139; 536/23.2

(58) Field of Classification Search .................. None
See application file for complete search history.

(56) References Cited

U.S. PATENT DOCUMENTS

| 5,712,152 A | 1/1998 | Dequin et al. |
| 2003/0032152 A1 | 2/2003 | Porro et al. |

FOREIGN PATENT DOCUMENTS

| FR | 2 692 591 A1 | 12/1993 |
| JP | 58-16688 A | 1/1983 |
| JP | 58-36394 A | 3/1983 |
| JP | 61-293387 A | 12/1986 |
| JP | 4-271787 A | 9/1992 |
| JP | 2001-29063 A | 2/2001 |
| JP | 2001-516584 A | 10/2001 |
| JP | 2002-136293 A | 5/2002 |
| JP | 2003-164294 A | 6/2003 |
| JP | 2003-164295 A | 6/2003 |
| JP | 2003-259878 A | 9/2003 |
| JP | 2003-334092 A | 11/2003 |
| JP | 2004-187643 A | 7/2004 |
| WO | WO 00/71738 A1 * | 11/2000 |
| WO | WO 03/027280 A1 | 4/2003 |

OTHER PUBLICATIONS

Kochhar et al. Cloning and overexpression of *Lactobacillus helveticus* D-lactate dehydrogenase gene in *Escherichia coli*. Eur J Biochem. Sep. 15, 1992;208(3):799-805.*
Bourel et al., "The response of *Leuconostoc mesenteroides* to low external oxidoreduction potential generated by hydrogen gas," J. Appl. Microbiol., 94: 280-288 (2003).
Branden et al., Introduction to Protein Structure, Garland Publishing, Inc., New York, p. 247 (1991).
Dartois et al., "Purification, properties and DNA sequence of the D-lactate dehydrogenase from *Leuconostoc mesenteroides subsp. cremoris*," Res. Microbiol., 146: 291-302 (1995).
Garland, "Purification and Properties of DL-Lactate Dehydrogenase from *Leuconostoc mesenteroides*," Arch. Biochem. Biophys., 157: 36-43 (1973).
Guo et al., "Protein tolerance to random amino acid change," PNAS, 101(25): 9205-9210 (2004).
Phalip et al., "Cloning of the D-Lactate Dehydrogenase Gene From *Leuconostoc mesenteroides* Subsp. cremoris," Biotechnology Letters, 16(3): 221-226 (1994).
International Search Report mailed Aug. 31, 2004, for International Patent App. No. PCT/JP2004/007317, filed May 21, 2004 (5 pages).
International Preliminary Report on Patentability completed Apr. 8, 2005, for International Patent App. No. PCT/JP2004/007317, filed May 21, 2004 (5 pages).
Supplementary European Search Report dated Jan. 8, 2007, for European Patent Application No. EP 04734403 (4 pages).
Restriction Requirement mailed Aug. 9, 2007, for U.S. Appl. No. 10/557,306, which has an International Filing Date of May 21, 2004 (8 pages).
Response to Restriction Requirement filed Sep. 7, 2007, for U.S. Appl. No. 10/557,306, which has an International Filing Date of May 21, 2004 (2 pages).
Office Action mailed Nov. 13, 2007, for U.S. Appl. No. 10/557,306, which has an International Filing Date of May 21, 2004 (24 pages).
Response to Office Action filed Feb. 8, 2008, for U.S. Appl. No. 10/557,306, which has an International Filing Date of May 21, 2004 (19 pages).

(Continued)

*Primary Examiner* — Yong D Pak
(74) *Attorney, Agent, or Firm* — Finnegan, Henderson, Farabow, Garrett & Dunner, LLP

(57) ABSTRACT

This invention provides a polynucleotide that encodes a protein having lactate dehydrogenase activity and such protein that can be used for producing D-lactic acid. This polynucleotide has the nucleotide sequence as shown in SEQ ID NO: 1 (a), and it hybridizes under stringent conditions with a probe comprising all or part of the nucleotide sequence as shown in SEQ ID NO: 1 or a complementary strand thereof and encodes a protein having D-lactate dehydrogenase activity (b).

15 Claims, 11 Drawing Sheets

OTHER PUBLICATIONS

Final Office Action mailed May 30, 2008, for U.S. Appl. No. 10/557,306, which has an International Filing Date of May 21, 2004 (9 pages).

NCBI Database Accession No. AAV68348, putative lactate dehydrogenase [Leuconostoc mesenteroides] (Nov. 28, 2004) (1 page).

NCBI Database Accession No. YP_819216, D-lactate dehydrogenase, LdhA [*Leuconostoc mesenteroides* subsp. *mesenteroides* ATCC 8293] (Jul. 23, 2008) (2 pages).

Catalog information for ATCC Deposit No. 8293 for *Leuconostoc mesenteroides* subsp. *mesenteroides* (Tsenkovskii) van Tieghem, printed Nov. 19, 2008 (2 pages).

Catalog information for ATCC Deposit No. 12291 for *Leuconostoc pseudomesenteroides* Farrow et al. deposited as *Leuconostoc mesenteroides* subsp. *mesenteroides* (Tsenkovskii) van Tieghem, printed Nov. 20, 2008 (2 pages).

Catalog information for ATCC Deposit No. 9135 for *Leuconostoc mesenteroides* subsp. *mesenteroides* (Tsenkovskii) van Tieghem, printed Nov. 26, 2008 (1 page).

National Institute of Technology and Evaluation (NITE) Biological Resource Center Catalogue detail information for NBRC No. 3426 for *Leuconostoc mesenteroides* subsp. *mesenteroides* (Tsenkovskii 1878) van Tieghem 1878, pritned Nov. 20, 2008 (2 pages).

Garvie, Ellen I., "Hybridization Between the Deoxyribonucleic Acids of Some Strains of Heterofermentative Lactic Acid Bacteria," International Journal of Systematic Bacteriology, 26(2): 116-122 (Apr. 1976).

Garvie, Ellen I., "Proposal of Neotype Strains for *Leuconostoc mesenteroides* (Tsenkovskii) van Tieghem, *Leuconostoc dextranicum* (Beijerinck) Hucker and Pederson, and *Leuconostoc cremoris* (Knudsen and Sørensen) Garvie," International Journal of Systematic Bacteriology, 29(2): 149-151 (Apr. 1979).

Garvie, Ellen I., "*Leuconostoc mesenteroides* subsp. *cremoris* (Knudsen and Sørensen) comb, nov. and *Leuconostoc mesenteroides* subsp. *dextranicum* (Beijerinck) comb. nov." International Journal of Systematic Bacteriology, 33(1): 118-119 (Jan. 1983).

Hontebeyrie et al., "Comparative immunological Relationships of Two Distinct Sets of Isofunctional Dehydrogenases in the Genus *Leuconostoc*," International Journal of Systematic Bacteriology, 25(1): 1-6 (Jan. 1975).

Skerman et al., "Approved Lists of Bacterial Names," Int. J. Syst. Bacteriol., 30: 225-420 (1980).

* cited by examiner

Fig. 1A

[ Nucleotide Sequence Homology Data ]

1st Nucleotide Sequence
  File Name       : pBLDHDORF
  Sequence Size  : 996

2nd Nucleotide Sequence
  File Name       : Leuconostoc mesenteroid
  Sequence Size  : 996

[ 968 / 997 bp]    INT/OPT.Score : <   3684/  3794 >

```
    1' ATGAAGATTTTTGCTTACGGCATTCGTGATGATGAAAAGCCATCACTTGAAGAATGGAAA
       ************************************************************
    1" ATGAAGATTTTTGCTTACGGCATTCGTGATGATGAAAAGCCATCACTTGAAGAATGGAAA

61' GCGGCTAACCCAGAGATTGAAGTGGACTACACACAAGAGCTATTGACACCTGAAACAGTT
       **********************************  ****************** *
   61" GCGGCTAACCCAGAGATTGAAGTGGACTACACACAAGAATTATTGACACCTGAAACAGCT

121' AAGTTGGCTGAGGGATCAGATTCAGCTGTTGTTTACCAACAACTGGACTATACACGTGAA
       **********************************  ******  ****************
  121" AAGTTGGCTGAGGGATCAGATTCAGCTGTTGTTTATCAACAATTGGACTATACACGTGAA

181' ACATTGACAGCTTTAGCTAACGTTGGTGTTACTAACTTGTCATTGCGTAACGTTGGTACA
       ************************************************************
  181" ACATTGACAGCTTTAGCTAACGTTGGTGTTACTAACTTGTCATTGCGTAACGTTGGTACA

241' GATAACATTGATTTTGATGCAGCACGTGAATTTAACTTTAACATTTCAAATGTTCCTGTT
       ************************************************************
  241" GATAACATTGATTTTGATGCAGCACGTGAATTTAACTTTAACATTTCAAATGTTCCTGTT

301' TATTCACCAAATGCTATTGCAGAACACTCAATGATTCAATTATCTCGTTTGCTACGTCGC
       ******************************  ****************************
  301" TATTCACCAAATGCTATTGCAGAACACTCAATGCTTCAATTATCTCGTTTGCTACGTCGC

361' ACGAAAGCATTGGATGCCAAAATTGCTAAGCACGACTTGCGCTGGGCACCAACAATTGGA
       ******************************** ******** ************ ****
  361" ACGAAAGCATTGGATGCCAAAATTGCTAAGCGAGACTTGCGTTGGGCACCAACAACTGGA
```

Fig. 1B

```
421'  CGTGAAATGCGTATGCAAACAGTTGGTGTTATTGGTACAGGCCATATTGGCCGTGTTGCT
      ************************************************ **********************
421"  CGTGAAATGCGTATGCAAACAGTTGGTGTTATTGGTACAGGTCATATTGGCCGTGTTGCT

481'  ATTAACATTTTGAAAGGCTTTGGGGCAAAGGTTATTGCTTATGATAAGTACCCAAATGCT
      ***************************** ****************** ****************
481"  ATTAACATTTTGAAAGGCTTTGGGGCCAAGGTTATTGCTTATGACAAGTACCCAAATGCT

541'  GAATTGCAAGCAGAAGGTTTGTACGTTGACACATTAGACGAATTATATGCACAAGCTGAT
      ***** ******************************************************
541"  GAATTACAAGCAGAAGGTTTGTACGTTGACACATTAGACGAATTATATGCACAAGCTGAT

601'  GCAATTTCATTGTATGTTCCTGGTGTGCCTGAAAACCATCATCTAATCAATGCAGAGGCT
      ***************************** ***************************** ***
601"  GCAATTTCATTGTATGTTCCTGGTGTACCTGAAAACCATCATCTAATCAATGCAGATGCT

661'  ATTGCTAAGATGAAGGATGGCGTGGTTATCATGAATGCTGCGCGTGGTAATTTGATGGAC
      ****************** **************** ************************
661"  ATTGCTAAGATGAAGGATGGTGTGGTTATCATGAACGCTGCGCGTGGTAATTTGATGGAC

721'  ATTGATGCTATTATTGATGGTTTGAATTCTGGTAAGATTTCAGACTTCGGTATGGACGTT
      **** ******************************************************
721"  ATTGACGCTATTATTGATGGTTTGAATTCTGGTAAGATTTCAGACTTCGGTATGGACGTT

781'  TATGAAAATGAAGTTGGCTTGTTCAATGAAGATTGGTCTGGTAAAGAATT-CCCAGATGC
      ***************** ******************************* ********
781"  TATGAAAATGAAGTT-GCTTGTTCAATGAAGATTGGTCTGGTAAAGAATTCCCCAGATGC

840'  TAAGATTGCTGACTTGATTTCACGCGAAAATGTATTGGTTACGCCACATACGGCTTTCTA
      ****************** ************ ** * ** ***** **********
840"  TAAGATTGCTGACTTGATTGCACGCGAAAATGTTATGATCACCCCACACACGGCTTTCTA

900'  TACAACTAAAGCTGTTCTAGAAATGGTTCACCAATCATTTGATGCAGCAGTTGCTTTCGC
      ************************************************************
900"  TACAACTAAAGCTGTTCTAGAAATGGTTCACCAATCATTTGATGCAGCAGTTGCTTTCGC

960'  CAAAGGTGAGAAGCCAGCTATTGCTGTTGAATATTAA
      *** *********************************
960"  CAAGGGTGAGAAGCCAGCTATTGCTGTTGAATATTAA
```

Fig. 2

[ GENETYX-MAC : Amino Acid Sequence Homology Data ]

1st Amino Acid Sequence
   File Name       : D-LDH AA. Leuconostoc mesenteroides
   Sequence Size  : 332

2nd Amino Acid Sequence
   File Name       : DATA BASE of Leuconostoc mesenteroides.a.a
   Sequence Size  : 331

[ 312 / 331 aa]
    INT/OPT.Score : < 1423/ 1423 >

```
   1' MKIFAYGIRDDEKPSLEEWKAANPEIEVDYTQELLTPETVKLAEGSDSAVVYQQLDYTRE
      ********************************, *******************
   1" MKIFAYGIRDDEKPSLEEWKAANPEIEVDYTQELLTPETAKLAEGSDSAVVYQQLDYTRE

61' TLTALANVGVTNLSLRNVGTDNIDFDAAREFNFNISNVPVYSPNAIAEHSMIQLSRLLRR
      *********************************************, *******
  61" TLTALANVGVTNLSLRNVGTDNIDFDAAREFNFNISNVPVYSPNAIAEHSMLQLSRLLRR

121' TKALDAKIAKHDLRWAPTIGREMRMQTVGVIGTGHIGRVAINILKGFGAKVIAYDKYPNA
      *********, *******, ****************************************
 121" TKALDAKIAKRDLRWAPTTGREMRMQTVGVIGTGHIGRVAINILKGFGAKVIAYDKYPNA

181' ELQAEGLYVDTLDELYAQADAISLYVPGVPENHHLINAEAIAKMKDGVVIMNAARGNLMD
      ***************************************, *******************
 181" ELQAEGLYVDTLDELYAQADAISLYVPGVPENHHLINADAIAKMKDGVVIMNAARGNLMD

241' IDAIIDGLNSGKISDFGMDVYENEVGLFNEDWSGKEFPDAKIADLISRENVLVTPHTAFY
      *******************,   . *. ********.****..*******
 241" IDAIIDGLNSGKISDFGMDVYENEVACSMKIGLVKNSPDAKIADLIARENVMITPHTAFY

301' TTKAVLEMVHQSFDAAVAFAKGEKPAIAVEY
      ******************************
 301" TTKAVLEMVHQSFDAAVAFAKGEKPAIAVEY
```

Yeast chromosomal DNA

SEQUENCE LISTING

```
<160> NUMBER OF SEQ ID NOS: 11

<210> SEQ ID NO 1
<211> LENGTH: 996
<212> TYPE: DNA
<213> ORGANISM: Leuconostoc mesenteroides
<220> FEATURE:
<221> NAME/KEY: CDS
<222> LOCATION: (1)..(996)

<400> SEQUENCE: 1 atg aag att ttt gct tac ggc att cgt gat gat gaa aag cca tca ctt        48
Met Lys Ile Phe Ala Tyr Gly Ile Arg Asp Asp Glu Lys Pro Ser Leu
1               5                  10                  15 gaa gaa tgg aaa gcg gct aac cca gag att gaa gtg gac tac aca caa        96
Glu Glu Trp Lys Ala Ala Asn Pro Glu Ile Glu Val Asp Tyr Thr Gln
            20                  25                  30 gag cta ttg aca cct gaa aca gtt aag ttg gct gag gga tca gat tca       144
Glu Leu Leu Thr Pro Glu Thr Val Lys Leu Ala Glu Gly Ser Asp Ser
        35                  40                  45 gct gtt gtt tac caa caa ctg gac tat aca cgt gaa aca ttg aca gct       192
Ala Val Val Tyr Gln Gln Leu Asp Tyr Thr Arg Glu Thr Leu Thr Ala
    50                  55                  60 tta gct aac gtt ggt gtt act aac ttg tca ttg cgt aac gtt ggt aca       240
Leu Ala Asn Val Gly Val Thr Asn Leu Ser Leu Arg Asn Val Gly Thr
65                  70                  75                  80 gat aac att gat ttt gat gca gca cgt gaa ttt aac ttt aac att tca       288
Asp Asn Ile Asp Phe Asp Ala Ala Arg Glu Phe Asn Phe Asn Ile Ser
                85                  90                  95 aat gtt cct gtt tat tca cca aat gct att gca gaa cac tca atg att       336
Asn Val Pro Val Tyr Ser Pro Asn Ala Ile Ala Glu His Ser Met Ile
            100                 105                 110 caa tta tct cgt ttg cta cgt cgc acg aaa gca ttg gat gcc aaa att       384
Gln Leu Ser Arg Leu Leu Arg Arg Thr Lys Ala Leu Asp Ala Lys Ile
        115                 120                 125
```

```
gct aag cac gac ttg cgc tgg gca cca aca att gga cgt gaa atg cgt    432
Ala Lys His Asp Leu Arg Trp Ala Pro Thr Ile Gly Arg Glu Met Arg
130                 135                 140 atg caa aca gtt ggt gtt att ggt aca ggc cat att ggc cgt gtt gct    480
Met Gln Thr Val Gly Val Ile Gly Thr Gly His Ile Gly Arg Val Ala
145                 150                 155                 160 att aac att ttg aaa ggc ttt ggg gca aag gtt att gct tat gat aag    528
Ile Asn Ile Leu Lys Gly Phe Gly Ala Lys Val Ile Ala Tyr Asp Lys
                165                 170                 175 tac cca aat gct gaa ttg caa gca gaa ggt ttg tac gtt gac aca tta    576
Tyr Pro Asn Ala Glu Leu Gln Ala Glu Gly Leu Tyr Val Asp Thr Leu
            180                 185                 190 gac gaa tta tat gca caa gct gat gca att tca ttg tat gtt cct ggt    624
Asp Glu Leu Tyr Ala Gln Ala Asp Ala Ile Ser Leu Tyr Val Pro Gly
        195                 200                 205 gtg cct gaa aac cat cat cta atc aat gca gag gct att gct aag atg    672
Val Pro Glu Asn His His Leu Ile Asn Ala Glu Ala Ile Ala Lys Met
    210                 215                 220 aag gat ggc gtg gtt atc atg aat gct gcg cgt ggt aat ttg atg gac    720
Lys Asp Gly Val Val Ile Met Asn Ala Ala Arg Gly Asn Leu Met Asp
225                 230                 235                 240 att gat gct att att gat ggt ttg aat tct ggt aag att tca gac ttc    768
Ile Asp Ala Ile Ile Asp Gly Leu Asn Ser Gly Lys Ile Ser Asp Phe
                245                 250                 255 ggt atg gac gtt tat gaa aat gaa gtt ggc ttg ttc aat gaa gat tgg    816
Gly Met Asp Val Tyr Glu Asn Glu Val Gly Leu Phe Asn Glu Asp Trp
            260                 265                 270 tct ggt aaa gaa ttc cca gat gct aag att gct gac ttg att tca cgc    864
Ser Gly Lys Glu Phe Pro Asp Ala Lys Ile Ala Asp Leu Ile Ser Arg
        275                 280                 285 gaa aat gta ttg gtt acg cca cat acg gct ttc tat aca act aaa gct    912
Glu Asn Val Leu Val Thr Pro His Thr Ala Phe Tyr Thr Thr Lys Ala
    290                 295                 300 gtt cta gaa atg gtt cac caa tca ttt gat gca gca gtt gct ttc gcc    960
Val Leu Glu Met Val His Gln Ser Phe Asp Ala Ala Val Ala Phe Ala
305                 310                 315                 320 aaa ggt gag aag cca gct att gct gtt gaa tat taa                    996
Lys Gly Glu Lys Pro Ala Ile Ala Val Glu Tyr
                325                 330
```

<210> SEQ ID NO 2
<211> LENGTH: 331
<212> TYPE: PRT
<213> ORGANISM: Leuconostoc mesenteroides

<400> SEQUENCE: 2

```
Met Lys Ile Phe Ala Tyr Gly Ile Arg Asp Asp Glu Lys Pro Ser Leu
1               5                   10                  15

Glu Glu Trp Lys Ala Ala Asn Pro Glu Ile Glu Val Asp Tyr Thr Gln
            20                  25                  30

Glu Leu Leu Thr Pro Glu Thr Val Lys Leu Ala Glu Gly Ser Asp Ser
        35                  40                  45

Ala Val Val Tyr Gln Gln Leu Asp Tyr Thr Arg Glu Thr Leu Thr Ala
    50                  55                  60

Leu Ala Asn Val Gly Val Thr Asn Leu Ser Leu Arg Asn Val Gly Thr
65                  70                  75                  80

Asp Asn Ile Asp Phe Asp Ala Ala Arg Glu Phe Asn Phe Asn Ile Ser
                85                  90                  95

Asn Val Pro Val Tyr Ser Pro Asn Ala Ile Ala Glu His Ser Met Ile
```

```
                100              105                110
Gln Leu Ser Arg Leu Leu Arg Arg Thr Lys Ala Leu Asp Ala Lys Ile
            115                 120                 125
Ala Lys His Asp Leu Arg Trp Ala Pro Thr Ile Gly Arg Glu Met Arg
        130                 135                 140
Met Gln Thr Val Gly Val Ile Gly Thr Gly His Ile Gly Arg Val Ala
145                 150                 155                 160
Ile Asn Ile Leu Lys Gly Phe Gly Ala Lys Val Ile Ala Tyr Asp Lys
                165                 170                 175
Tyr Pro Asn Ala Glu Leu Gln Ala Glu Gly Leu Tyr Val Asp Thr Leu
            180                 185                 190
Asp Glu Leu Tyr Ala Gln Ala Asp Ala Ile Ser Leu Tyr Val Pro Gly
        195                 200                 205
Val Pro Glu Asn His His Leu Ile Asn Ala Glu Ala Ile Ala Lys Met
    210                 215                 220
Lys Asp Gly Val Val Ile Met Asn Ala Ala Arg Gly Asn Leu Met Asp
225                 230                 235                 240
Ile Asp Ala Ile Ile Asp Gly Leu Asn Ser Gly Lys Ile Ser Asp Phe
                245                 250                 255
Gly Met Asp Val Tyr Glu Asn Glu Val Gly Leu Phe Asn Glu Asp Trp
            260                 265                 270
Ser Gly Lys Glu Phe Pro Asp Ala Lys Ile Ala Asp Leu Ile Ser Arg
        275                 280                 285
Glu Asn Val Leu Val Thr Pro His Thr Ala Phe Tyr Thr Thr Lys Ala
    290                 295                 300
Val Leu Glu Met Val His Gln Ser Phe Asp Ala Ala Val Ala Phe Ala
305                 310                 315                 320
Lys Gly Glu Lys Pro Ala Ile Ala Val Glu Tyr
                325                 330

<210> SEQ ID NO 3
<211> LENGTH: 996
<212> TYPE: DNA
<213> ORGANISM: Leuconostoc mesenteroides
<220> FEATURE:
<221> NAME/KEY: CDS
<222> LOCATION: (1)..(996)

<400> SEQUENCE: 3 atg aag att ttt gct tac ggc att cgt gat gat gaa aag cca tca ctt    48
Met Lys Ile Phe Ala Tyr Gly Ile Arg Asp Asp Glu Lys Pro Ser Leu
1               5                   10                  15 gaa gaa tgg aaa gcg gct aac cca gag att gaa gtg gac tac aca caa    96
Glu Glu Trp Lys Ala Ala Asn Pro Glu Ile Glu Val Asp Tyr Thr Gln
            20                  25                  30 gaa tta ttg aca cct gaa aca gct aag ttg gct gag gga tca gat tca   144
Glu Leu Leu Thr Pro Glu Thr Ala Lys Leu Ala Glu Gly Ser Asp Ser
        35                  40                  45 gct gtt gtt tat caa caa ttg gac tat aca cgt gaa aca ttg aca gct   192
Ala Val Val Tyr Gln Gln Leu Asp Tyr Thr Arg Glu Thr Leu Thr Ala
    50                  55                  60 tta gct aac gtt ggt gtt act aac ttg tca ttg cgt aac gtt ggt aca   240
Leu Ala Asn Val Gly Val Thr Asn Leu Ser Leu Arg Asn Val Gly Thr
65                  70                  75                  80 gat aac att gat ttt gat gca gca cgt gaa ttt aac ttt aac att tca   288
Asp Asn Ile Asp Phe Asp Ala Ala Arg Glu Phe Asn Phe Asn Ile Ser
                85                  90                  95 aat gtt cct gtt tat tca cca aat gct att gca gaa cac tca atg ctt   336
```

```
                  Asn Val Pro Val Tyr Ser Pro Asn Ala Ile Ala Glu His Ser Met Leu
                              100                 105                 110 caa tta tct cgt ttg cta cgt cgc acg aaa gca ttg gat gcc aaa att              384
Gln Leu Ser Arg Leu Leu Arg Arg Thr Lys Ala Leu Asp Ala Lys Ile
            115                 120                 125 gct aag cga gac ttg cgt tgg gca cca aca act gga cgt gaa atg cgt              432
Ala Lys Arg Asp Leu Arg Trp Ala Pro Thr Thr Gly Arg Glu Met Arg
130                 135                 140 atg caa aca gtt ggt gtt att ggt aca ggt cat att ggc cgt gtt gct              480
Met Gln Thr Val Gly Val Ile Gly Thr Gly His Ile Gly Arg Val Ala
145                 150                 155                 160 att aac att ttg aaa ggc ttt ggg gcc aag gtt att gct tat gac aag              528
Ile Asn Ile Leu Lys Gly Phe Gly Ala Lys Val Ile Ala Tyr Asp Lys
                165                 170                 175 tac cca aat gct gaa tta caa gca gaa ggt ttg tac gtt gac aca tta              576
Tyr Pro Asn Ala Glu Leu Gln Ala Glu Gly Leu Tyr Val Asp Thr Leu
            180                 185                 190 gac gaa tta tat gca caa gct gat gca att tca ttg tat gtt cct ggt              624
Asp Glu Leu Tyr Ala Gln Ala Asp Ala Ile Ser Leu Tyr Val Pro Gly
            195                 200                 205 gta cct gaa aac cat cat cta atc aat gca gat gct att gct aag atg              672
Val Pro Glu Asn His His Leu Ile Asn Ala Asp Ala Ile Ala Lys Met
210                 215                 220 aag gat ggt gtg gtt atc atg aac gct gcg cgt ggt aat ttg atg gac              720
Lys Asp Gly Val Val Ile Met Asn Ala Ala Arg Gly Asn Leu Met Asp
225                 230                 235                 240 att gac gct att att gat ggt ttg aat tct ggt aag att tca gac ttc              768
Ile Asp Ala Ile Ile Asp Gly Leu Asn Ser Gly Lys Ile Ser Asp Phe
                245                 250                 255 ggt atg gac gtt tat gaa aat gaa gtt gct tgt tca atg aag att ggt              816
Gly Met Asp Val Tyr Glu Asn Glu Val Ala Cys Ser Met Lys Ile Gly
            260                 265                 270 ctg gta aag aat tcc cca gat gct aag att gct gac ttg att gca cgc              864
Leu Val Lys Asn Ser Pro Asp Ala Lys Ile Ala Asp Leu Ile Ala Arg
            275                 280                 285 gaa aat gtt atg atc acc cca cac acg gct ttc tat aca act aaa gct              912
Glu Asn Val Met Ile Thr Pro His Thr Ala Phe Tyr Thr Thr Lys Ala
            290                 295                 300 gtt cta gaa atg gtt cac caa tca ttt gat gca gca gtt gct ttc gcc              960
Val Leu Glu Met Val His Gln Ser Phe Asp Ala Ala Val Ala Phe Ala
305                 310                 315                 320 aag ggt gag aag cca gct att gct gtt gaa tat taa                              996
Lys Gly Glu Lys Pro Ala Ile Ala Val Glu Tyr
                325                 330

<210> SEQ ID NO 4
<211> LENGTH: 331
<212> TYPE: PRT
<213> ORGANISM: Leuconostoc mesenteroides

<400> SEQUENCE: 4

Met Lys Ile Phe Ala Tyr Gly Ile Arg Asp Asp Glu Lys Pro Ser Leu
1               5                   10                  15

Glu Glu Trp Lys Ala Ala Asn Pro Glu Ile Glu Val Asp Tyr Thr Gln
            20                  25                  30

Glu Leu Leu Thr Pro Gly Thr Ala Lys Leu Ala Glu Gly Ser Asp Ser
        35                  40                  45

Ala Val Val Tyr Gln Gln Leu Asp Tyr Thr Arg Glu Thr Leu Thr Ala
    50                  55                  60

Leu Ala Asn Val Gly Val Thr Asn Leu Ser Leu Arg Asn Val Gly Thr
```

```
                65                  70                  75                  80
Asp Asn Ile Asp Phe Asp Ala Ala Arg Glu Phe Asn Phe Asn Ile Ser
                    85                  90                  95

Asn Val Pro Val Tyr Ser Pro Asn Ala Ile Ala Glu His Ser Met Leu
                100                 105                 110

Gln Leu Ser Arg Leu Leu Arg Arg Thr Lys Ala Leu Asp Ala Lys Ile
            115                 120                 125

Ala Lys Arg Asp Leu Arg Trp Ala Pro Thr Thr Gly Arg Glu Met Arg
130                 135                 140

Met Gln Thr Val Gly Val Ile Gly Thr Gly His Ile Gly Arg Val Ala
145                 150                 155                 160

Ile Asn Ile Leu Lys Gly Phe Gly Ala Lys Val Ile Ala Tyr Asp Lys
                165                 170                 175

Tyr Pro Asn Ala Glu Leu Gln Ala Glu Gly Leu Tyr Val Asp Thr Leu
            180                 185                 190

Asp Glu Leu Tyr Ala Gln Ala Asp Ala Ile Ser Leu Tyr Val Pro Gly
        195                 200                 205

Val Pro Glu Asn His His Leu Ile Asn Ala Asp Ala Ile Ala Lys Met
    210                 215                 220

Lys Asp Gly Val Val Ile Met Asn Ala Ala Arg Gly Asn Leu Met Asp
225                 230                 235                 240

Ile Asp Ala Ile Ile Asp Gly Leu Asn Ser Gly Lys Ile Ser Asp Phe
                245                 250                 255

Gly Met Asp Val Tyr Glu Asn Glu Val Ala Cys Ser Met Lys Ile Gly
            260                 265                 270

Leu Val Lys Asn Ser Pro Asp Ala Lys Ile Ala Asp Leu Ile Ala Arg
        275                 280                 285

Glu Asn Val Met Ile Thr Pro His Thr Ala Phe Tyr Thr Thr Lys Ala
    290                 295                 300

Val Leu Glu Met Val His Gln Ser Phe Asp Ala Ala Val Ala Phe Ala
305                 310                 315                 320

Lys Gly Glu Lys Pro Ala Ile Ala Val Glu Tyr
                325                 330

<210> SEQ ID NO 5
<211> LENGTH: 971
<212> TYPE: DNA
<213> ORGANISM: Saccharomyces cerevisiae

<400> SEQUENCE: 5
aagggtagcc tccccataac ataaactcaa taaaatatat agtcttcaac ttgaaaaagg      60
aacaagctca tgcaaagagg tggtacccgc acgccgaaat gcatgcaagt aacctattca     120
aagtaatatc tcatacatgt ttcatgaggg taacaacatg cgactgggtg agcatatgct     180
ccgctgatgt gatgtgcaag ataaacaagc aagacggaaa ctaacttctt cttcatgtaa     240
taaacacacc ccgcgtttat ttacctatct ttaaacttca acaccttata tcataactaa     300
tatttcttga gataagcaca ctgcacccat accttcctta aaagcgtagc ttccagtttt     360
tggtggttcc ggcttccttc ccgattccgc ccgctaaacg catattttg ttgcctggtg      420 gcatttgcaa aatgcataac ctatgcattt aaaagattat gtatgctctt ctgacttttc     480
gtgtgatgaa gctcgtggaa aaaatgaata atttatgaat ttgagaacaa ttctgtgttg     540
ttacggtatt ttactatgga ataattaatc aattgaggat tttatgcaaa tatcgtttga     600
atatttttcc gacccttgta gtactttttct tcataattgc ataatattgt ccgctgcccg    660
```

-continued

```
tttttctgtt agacggtgtc ttgatctact tgctatcgtt caacaccacc ttatttctta    720 actattttt tttagctca tttgaatcag cttatggtga tggcacattt ttgcataaac     780
ctagctgtcc tcgttgaaca taggaaaaaa aaatatatta acaaggctct ttcactctcc   840
ttgcaatcag atttgggttt gttcccttta tttcatatt tcttgtcata ttcctttctc    900
aattattatt ttctactcat aaccacacgc aaaataacac agtcaaatca atcaaagatc   960
ccccaattct c                                                        971
```

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6

```
atgaagattt ttgcttacgg c                                              21
```

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7

```
atcttaatat tcaacagcaa tagc                                           24
```

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 8

```
atatatggat ccgcgtttat ttacctatct c                                   31
```

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 9

```
atatatgaat tctttgattg atttgactgt g                                   31
```

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 10

```
atatatctcg aggccagcta acttcttggt cgac                                34
```

<210> SEQ ID NO 11
<211> LENGTH: 31
<212> TYPE: DNA
<213> ORGANISM: Artificial Sequence -continued

```
<220> FEATURE:
<223> OTHER INFORMATION: Description of Artificial Sequence: Primer

<400> SEQUENCE: 11
atatatgggc cccccctcga ggtccccct c                                        31
```

DNA ENCODING A PROTEIN HAVING D-LACTATE DEHYDROGENASE ACTIVITY AND USES THEREOF

This application is a continuation of U.S. patent application Ser. No. 10/557,306, filed Nov. 18, 2005, now abandoned, which is a national stage application of PCT International Application No. PCT/JP2004/007317, filed May 21, 2004, which claims priority to Japanese Application No. 2003-145085, filed May 22, 2003, all of which are incorporated herein by reference.

TECHNICAL FIELD

The present invention relates to D-lactic acid and a technique for producing a polymer utilizing D-lactic acid. More particularly, the present invention relates to a protein having D-lactate dehydrogenase activity that is suitable for allowing yeast to produce D-lactic acid, DNA having a nucleotide sequence encoding such protein, and uses thereof.

BACKGROUND ART

With advances in recombinant DNA technology, a technique for obtaining gene products of interest has been developed. Such technique is realized by allowing foreign genes to be expressed in hosts such as microorganisms, molds, animals, plants, or insects and by allowing the resulting transformants to multiply. When a technique of yeast culturing is employed, for example, a large quantity of gene products of interest can be produced via fermentative production.

Effective production of lactic acid, which is a starting material of plant-derived plastics, has been awaited in recent years from the viewpoint of "carbon neutrality."

Lactic acid is classified into L-lactic acid and D-lactic acid, which are optical isomers. A technique for fermentatively producing D-lactic acid has been known, whereby D-lactic acid is fermentatively produced using lactic acid bacteria capable of producing D-lactic acid in a medium containing brewers' yeast (JP Patent Publication (Kokai) No. 58-16688 A (1983)). Also, a technique that involves the use of *Lactobacillus bulgaricus* has been known (JP Patent Publication (Kokai) No. 58-36394 A (1983)). A technique for obtaining D-lactic acid with high optical purity has also been disclosed (JP Patent Publication (Kokai) Nos. 61-293387 A (1986), 4-271787 A (1992), and 2001-29063 (A)). Such microorganisms capable of producing lactic acid have not been suitable for industrial production of lactic acid due to the slow rates of production and the necessity for complicated medium compositions.

Another technique has also been disclosed, whereby a lactate dehydrogenase gene is incorporated into a yeast strain lacking the capacity for ethanol production or having a reduced capacity for ethanol production, and the resulting recombinant product is used to produce lactic acid (JP Patent Publication (Kokai) No. 2001-516584 (A)). This technique, however, merely discloses the production of L-lactic acid. Further, a technique for producing D-lactic acid has been disclosed, whereby a D-lactate dehydrogenase gene is introduced into yeast that has a high capacity for producing pyruvic acid (JP Patent Publication (Kokai) No. 2002-136293 (A)). This technique is, however, focused on highly concentrated pyruvic acid in a yeast strain having a high capacity for producing pyruvic acid. Accordingly, production by general yeast is not described therein.

The present invention is directed to providing a polynucleotide encoding a protein that can be utilized for producing D-lactic acid having lactate dehydrogenase activity, and it is also directed to providing such protein. In addition, the present invention is directed to providing an excellent system for producing D-lactic acid utilizing such polynucleotide and a technique for effectively producing D-lactic acid.

DISCLOSURE OF THE INVENTION

In order to attain the above objects, the present inventors have searched for D-lactate dehydrogenase and genes that allow expression of such enzyme. As a result, they discovered a transformed line that exhibits an excellent capacity for producing D-lactic acid. More specifically, they discovered a protein that can positively affect the production of D-lactic acid and that has D-lactate dehydrogenase activity, DNA that encodes a protein having such enzyme activity, and a transformant prepared from such DNA. Further, they discovered a method for producing D-lactic acid using the same and a method for producing polylactic acid.

On the basis of the above findings, the present invention provides the following.

(1) A polynucleotide as described in any of the following (a) to (g):

(a) a polynucleotide comprising the nucleotide sequence as shown in SEQ ID NO: 1;

(b) a polynucleotide that hybridizes under stringent conditions with a probe comprising all or part of the nucleotide sequence as shown in SEQ ID NO: 1 or a complementary strand thereof and that encodes a protein having D-lactate dehydrogenase activity;

(c) a polynucleotide that encodes a protein consisting of the amino acid sequence as shown in SEQ ID NO: 2;

(d) a polynucleotide that encodes a protein consisting of an amino acid sequence derived from the amino acid sequence as shown in SEQ ID NO: 2 by substitution, deletion, insertion, or addition of one or several amino acid residues and having D-lactate dehydrogenase activity;

(e) a polynucleotide that encodes a protein having 70% or higher homology to the amino acid sequence as shown in SEQ ID NO: 2 and having D-lactate dehydrogenase activity;

(f) a polynucleotide that encodes a protein having an amino acid sequence derived from the amino acid sequence as shown in SEQ ID NO: 4 by substitution of one or more amino acid residues selected from the list of amino acid residue substitutions shown in Table 1 and having D-lactate dehydrogenase activity:

TABLE 1

List of amino acid residue substitutions

| Substitution type | Position of substitution | Amino acid substituent |
|---|---|---|
| 1 | 40 | Valine (Val) |
| 2 | 112 | Isoleucine (Ile) |
| 3 | 131 | Histidine (His) |
| 4 | 139 | Isoleucine (Ile) |
| 5 | 181 | Glutamic acid (Glu) |
| 6 | 266 | Glycine (Gly) |
| 7 | 267 | Leucine (Leu) |
| 8 | 268 | Phenylalanine (Phe) |
| 9 | 269 | Asparagine (Asn) |
| 10 | 270 | Glutamic acid (Glu) |
| 11 | 271 | Aspartic acid (Asp) |
| 12 | 272 | Tryptophan (Trp) |
| 13 | 273 | Serine (Ser) |
| 14 | 274 | Glycine (Gly) |
| 15 | 276 | Glutamic acid (Glu) |
| 16 | 277 | Phenylalanine (Phe) |
| 17 | 287 | Serine (Ser) |

TABLE 1-continued

List of amino acid residue substitutions

| Substitution type | Position of substitution | Amino acid substituent |
|---|---|---|
| 18 | 292 | Leucine (Leu) |
| 19 | 293 | Valine (Val) | wherein positions of substitution are indicated as the positions from methionine, which corresponds to the initiation codon; or (g) a polynucleotide that encodes a protein having an amino acid sequence containing at least amino acid residues 78 and 79, 152 to 175, 235, and 296 of the amino acid sequence as shown in SEQ ID NO: 2 and having D-lactate dehydrogenase activity.

(2) A protein as described in any of the following (h) to (l):

(h) a protein that consists of the amino acid sequence as shown in SEQ ID NO: 2 of the Sequence Listing;

(i) a protein that consists of an amino acid sequence derived from the amino acid sequence as shown in SEQ ID NO: 2 by substitution, deletion, insertion, or addition of one or several amino acid residues and that has D-lactate dehydrogenase activity;

(j) a protein that has 70% or higher homology to the amino acid sequence as shown in SEQ ID NO: 2 and that has D-lactate dehydrogenase activity;

(k) a protein that has an amino acid sequence derived from the amino acid sequence as shown in SEQ ID NO: 4 by substitution of one or more amino acid residues selected from the list of amino acid residue substitutions shown in Table 1 and that has D-lactate dehydrogenase activity; or (l) a protein that has an amino acid sequence containing at least amino acid residues 78 and 79, 152 to 175, 235, and 296 of the amino acid sequence as shown in SEQ ID NO: 2 and that has D-lactate dehydrogenase activity.

(3) A DNA construct that comprises a DNA segment comprising DNA according to (1) and a DNA segment comprising DNA that encodes a promoter or a homolog thereof.

(4) The DNA construct according to (3), wherein the promoter is of the pyruvate decarboxylase gene.

(5) The DNA construct according to (3) or (4), wherein the promoter is of the pyruvate decarboxylase 1 gene of *Saccharomyces*.

(6) The DNA construct according to (5), wherein the promoter is of the pyruvate decarboxylase 1 gene of *Saccharomyces cerevisae*.

(7) A transformant that carries the DNA according to (1) in an expressible manner in a host.

(8) The transformant according to (7), wherein the host is a microorganism selected from the group consisting of eukaryotic microorganisms including yeast and fungi and prokaryotic microorganisms including lactic acid bacteria, *Escherichiai* bacteria, and *Bacillus* bacteria.

(9) The transformant according to (7) or (8), wherein the DNA is carried in an expressible manner under the control of a promoter or a homolog thereof.

(10) The transformant according to (9), wherein the promoter is of the pyruvate decarboxylase gene.

(11) The transformant according to (9) or (10), wherein the promoter is of the pyruvate decarboxylase 1 gene of *Saccharomyces*.

(12) The transformant according to (11), wherein the DNA is carried in an expressible manner under the control of the promoter of the host pyruvate decarboxylase 1 gene.

(13) The transformant according to any one of (7) to (12), wherein the host microorganism is *Saccharomyces cerevisae*.

(14) A method for producing D-lactic acid comprising steps of:

culturing the transformant according to any one of (7) to (13); and recovering at least one member selected from the group consisting of D-lactic acid, a salt thereof, and a derivative thereof from the culture product.

(15) A method for producing a lactic acid polymer comprising steps of:

culturing the transformant according to any one of (7) to (13);

recovering at least one member selected from the group consisting of D-lactic acid, a salt thereof, and a derivative thereof from the culture product; and producing a lactic acid polymer using the recovered D-lactic acid or a derivative thereof as at least one polymerization material.

This description includes part or all of the contents as disclosed in the description and/or drawings of Japanese Patent Application No. 2003-145085, which is a priority document of the present application.

BRIEF DESCRIPTION OF THE DRAWINGS

FIG. 1A shows the homology data of the nucleotide sequence as shown in SEQ ID NO: 1 and the nucleotide sequence as shown in SEQ ID NO: 3.

FIG. 1B is a continuation of FIG. 1A, which shows the homology data of the nucleotide sequence as shown in SEQ ID NO: 1 and the nucleotide sequence as shown in SEQ ID NO: 3.

FIG. 2 shows the homology data of the amino acid sequence as shown in SEQ ID NO: 2 and the amino acid sequence as shown in SEQ ID NO: 4.

EMBODIMENTS OF THE INVENTION

Figure 3:
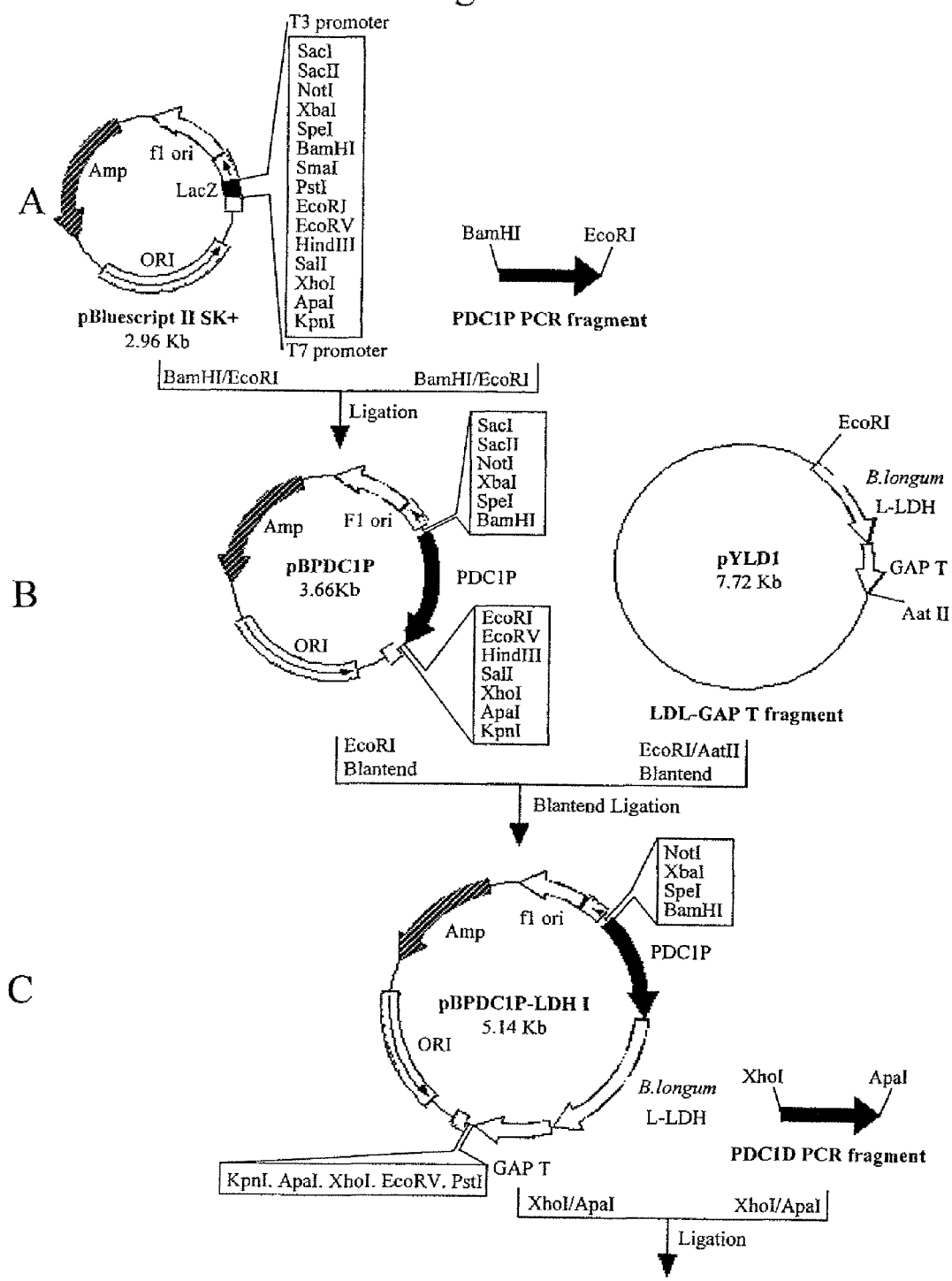
FIG. 3 shows a part of a procedure for constructing a pBTRP-PDC1-DLDHME vector.

The polynucleotide according to the present invention comprises a nucleotide sequence that encodes a protein having D-lactate dehydrogenase (D-LDH) activity.

Use of the polynucleotide according to the present invention can result in the production of a transformant that allows the expression of the aforementioned protein and a transformant that produces D-lactic acid. Also, D-lactic acid can be produced via an enzyme reaction system that involves the use of a protein encoded by the polynucleotide according to the present invention.

According to the present invention, a novel source for a starting material of D-lactic acid can be provided. Also, D-lactic acid can be produced with high selectivity or high efficiency according to the present invention.

Accordingly, the present invention can provide a technique for producing a lactic acid polymer with the use of an enzyme reaction system that involves the use of the protein according to the present invention or D-lactic acid produced by a transformant that allows the expression of the protein according to the present invention.

Hereafter, the polynucleotides, the protein, the transformant, the method for producing D-lactic acid according to the present invention, or the like are described.

The polynucleotide according to the present invention can include any of the following.

That is:

(a) a polynucleotide that comprises the nucleotide sequence as shown in SEQ ID NO: 1;

(b) a polynucleotide that hybridizes under stringent conditions with a probe comprising all or part of the nucleotide sequence as shown in SEQ ID NO: 1 or a complementary strand thereof and that encodes a protein having D-lactate dehydrogenase (D-LDH) activity;

(c) a polynucleotide that encodes a protein having the amino acid sequence as shown in SEQ ID NO: 2;

(d) a polynucleotide that encodes a protein consisting of an amino acid sequence derived from the amino acid sequence as shown in SEQ ID NO: 2 by substitution, deletion, insertion, or addition of one or several amino acid residues and having D-lactate dehydrogenase activity;

(e) a polynucleotide that has encodes a protein having 70% or higher homology to the amino acid sequence as shown in SEQ ID NO: 2 and having D-lactate dehydrogenase activity;

(f) a polynucleotide that encodes a protein having an amino acid sequence derived from the amino acid sequence as shown in SEQ ID NO: 4 by substitution of one or more amino acid residues selected from the list of amino acid residue substitutions shown in Table 1 and having D-lactate dehydrogenase activity; or (g) a polynucleotide that encodes a protein having an amino acid sequence containing at least amino acid residues 78 and 79, 152 to 175, 235, and 296 of the amino acid sequence as shown in SEQ ID NO: 2 and having D-lactate dehydrogenase activity.

The polynucleotide that consists of the nucleotide sequence as shown in SEQ ID NO: 1 according to the present invention encodes a protein that has the amino acid sequence as shown in SEQ ID NO: 2. Also, such polynucleotide is derived from *Leuconostoc mesenteroides*, which is a lactic acid bacterium. More specifically, such polynucleotide is derived from the *Leuconostoc mesenteroides* strain IFO3426 (registered with the Institute for Fermentation).

The sequence of this polynucleotide differs from the sequence registered with GenBank (GenBank Accession No. L29327) in terms of 27-bp nucleotides. As a result, the amino acid sequence (SEQ ID NO: 2) that is encoded by the polynucleotide differs from the amino acid sequence (SEQ ID NO: 4) based on the registered nucleotide sequence in terms of 19 amino acid residues. The nucleotide sequence as shown in SEQ ID NO: 1 shows 97.3% homology to the nucleotide sequence as shown in SEQ ID NO: 3. The amino acid sequence as shown in SEQ ID NO: 2 shows 94.3% homology to the amino acid sequence as shown in SEQ ID NO: 4. Such homology is calculated using Genetyx-mac ver. 10.1 (Software Development Co., Ltd.).

The present invention relates to a polynucleotide that encodes a protein having D-LDH activity. In the present invention, such polynucleotide may be a naturally occurring one such as DNA or RNA. Alternatively, such polynucleotide may contain an artificially synthesized nucleotide derivative. It may be single-stranded or it may have a complementary strand.

According to an embodiment of the present invention, the polynucleotide has the nucleotide sequence as shown in SEQ ID NO: 1. The polynucleotide as shown in SEQ ID NO: 1 encodes a protein having the amino acid sequence as shown in SEQ ID NO: 2.

According to another embodiment of the polynucleotide according to the present invention, a polynucleotide encodes a protein having the amino acid sequence as shown in SEQ ID NO: 2. A polynucleotide having a nucleotide sequence that encodes the amino acid sequence as shown in SEQ ID NO: 2 is sufficient.

According to a further embodiment of the present invention, the polynucleotide consists of an amino acid sequence derived from the amino acid sequence as shown in SEQ ID NO: 2 by substitution, deletion, insertion, or addition of one or several amino acid residues and has a nucleotide sequence encoding a protein having D-LDH activity.

A polynucleotide that has an amino acid sequence derived from the amino acid sequence as shown in SEQ ID NO: 2 by substitution, deletion, insertion, or addition of one or several amino acid residues is deduced to have D-LDH activity equivalent to that of a polynucleotide that has the amino acid sequence as shown in SEQ ID NO: 2. This is because the D-LDH activity resulting from the amino acid sequence as shown in SEQ ID NO: 2 is deduced to be equivalent to that resulting from an amino acid sequence derived from the former by substitution, deletion, insertion, or addition of one or several amino acid residues. A person skilled in the art can ordinarily select a protein having D-LDH activity, which can be sufficiently utilized in the present invention, by such amino acid substitution or the like.

A person skilled in the art can adequately introduce mutation such as substitution, deletion, insertion, and/or addition into a polynucleotide having the nucleotide sequence as shown in SEQ ID NO: 1 via site-directed mutagenesis (Nucleic Acid Res. 10, pp. 6487, 1982; Methods in Enzymol., 100, pp. 448, 1983; Molecular Cloning, 2nd Ed., Cold Spring Harbor Laboratory Press, 1989; PCR: A Practical Approach, IRL Press, pp. 200, 1991) or via other means. Preferably, "several amino acids" are approximately 2 to 10 amino acid residues, and more preferably approximately 2 to 4 amino acid residues.

According to a further embodiment of the present invention, the polynucleotide hybridizes under stringent conditions with a probe comprising all or part of the nucleotide sequence as shown in SEQ ID NO: 1 or a complementary strand thereof and encodes a protein having D-lactate dehydrogenase activity. A probe that can hybridize under stringent conditions with such polynucleotide comprises at least one DNA sequence constituted by any of 20 or more, and preferably 30 or more (for example, 40, 60, or 100) continuous nucleotides, of the sequence as shown in SEQ ID NO: 1. The polynucleotide can hybridize under stringent conditions with DNA as shown in SEQ ID NO: 1 or such probe. Under stringent conditions, for example, hybridization is carried out in the presence of 50% formaldehyde at approximately 37° C. Under more stringent conditions, hybridization is carried out at approximately 42° C. Under further stringent conditions, hybridization is carried out in the presence of formaldehyde at approximately 65° C.

An example of the polynucleotide that can hybridize under stringent conditions with DNA consisting of the nucleotide sequence as shown in SEQ ID NO: 1 or a probe is a polynucleotide that has a nucleotide sequence similar to the nucleotide sequence as shown in SEQ ID NO: 1. Such polynucleotide is highly likely to encode a protein that has functions equivalent to those of a protein consisting of the amino acid sequence as shown in SEQ ID NO: 2.

According to a further embodiment of the present invention, the polynucleotide encodes a protein that shows 70% or higher, preferably 80% or higher, more preferably 90% or higher, and further preferably 95% or higher homology to the amino acid sequence as shown in SEQ ID NO: 2, and that has D-lactate dehydrogenase activity. Protein homology search can be carried out using the gene-analyzing programs BLAST, FASTA, or the like. The term "homology" used herein refers to the identity observed through these programs.

The polynucleotide according to the present invention encodes a protein that has an amino acid sequence derived from the amino acid sequence as shown in SEQ ID NO: 4 by substitution of one or more amino acid residues selected from the list of amino acid residue substitutions shown in Table 1 and that has D-lactate dehydrogenase activity. The amino acid sequence as shown in SEQ ID NO: 4 is the sequence of D-LDH of *Leuconostoc mesenteroides* registered with GenBank (GenBank Accession No. L29327). The amino acid sequence as shown in SEQ ID NO: 2 is derived from the amino acid sequence as shown in SEQ ID NO: 4 via all substitutions indicated in the list of amino acid residue substitutions shown in Table 1. Even if the amino acid sequence does not have all the substitutions, however, a protein having D-LDH activity that may be utilized in the present invention can be obtained. The number of substitutions is preferably 2 or more, more preferably 11 or more, and further preferably 19 or more.

In the list of amino acid residue substitutions shown in Table 1, the amino acid substitutions indicated by substitution types 1 to 19 are preferable. The amino acid substitutions indicated by substitution types 6 to 16 are more preferable.

According to a further embodiment of the present invention, the polynucleotide encodes a protein that has an amino acid sequence containing at least amino acid residues 78 and 79, 152 to 175, 235, and 296 of the amino acid sequence as shown in SEQ ID NO: 2 and that has D-LDH activity. Amino acid residues 78 and 79, 152 to 175, 235, and 296 are considered to be characteristic of the amino acid sequence as shown in SEQ ID NO: 2. When a polynucleotide contains such amino acid sequence and has D-LDH activity, it can be said to be a preferable polynucleotide according to the present invention. More preferably, a polynucleotide has a histidine residue at position 296 as an active center and the coenzyme NADH binding domain constituted by amino acid residues 152 to 175 of the amino acid sequence as shown in SEQ ID NO: 2.

As described above, a polynucleotide of the present invention may be a polynucleotide that has functions equivalent to those of a protein encoded by the aforementioned protein, except the polynucleotide consisting of or comprising the nucleotide sequence as shown in SEQ ID NO: 1

The polynucleotide of the present invention can be obtained via various techniques as mentioned above. In addition, it can be chemically synthesized, or it can be obtained via PCR cloning, hybridization, or the like from other organisms based on the nucleotide sequence as shown in SEQ ID NO: 1. For example, a polynucleotide can be isolated from a protein derived from prokaryotic organisms such as lactic acid bacteria, *Escherichia coli* bacteria, *Bacillus subtilis* bacteria, or fungi or proteins derived from eukaryotic organisms such as yeast or octopus. Alternatively, the method of Fujimoto et al. that has been known as a method for synthesizing long-chain DNA can be adopted (Hideya Fujimoto, "Gousei idenshi no sakuseihou (Production of synthetic genes)," Shokubutsu saibo kogaku (Plant Cell Technology), Series 7, Shokubutsu no PCR jikken purotokoru (Protocol of plant PCR experiments), 1997, pp. 95-100, Shujunsha).

In the present invention, the polynucleotide may not be necessarily a homolog of the polynucleotide consisting of the nucleotide sequence as shown in SEQ ID NO: 1. This is because the transformant according to the present invention into which such polynucleotide has been introduced is useful for producing D-LDH and D-lactic acid.

For example, regardless of whether or not a polynucleotide has the nucleotide sequence as shown in SEQ ID NO: 1 or is a homolog thereof, a polynucleotide that encodes a protein having D-LDH activity derived from prokaryotic organisms such as lactic acid bacteria, *Escherichia coli* bacteria, *Bacillus subtilis* bacteria, or fungi or proteins having D-LDH activity derived from eukaryotic organisms such as yeast or octopus can also be employed.

(Protein)

The protein according to the present invention consists of or comprises the amino acid sequence as shown in SEQ ID NO: 2. Such protein is a preferable embodiment of the present invention.

According to another embodiment of the present invention, the protein consists of an amino acid sequence derived from the amino acid sequence as shown in SEQ ID NO: 2 by substitution, deletion, insertion, or addition of one or several amino acid residues and has D-lactate dehydrogenase (D-LDH) activity. According to a further embodiment, the protein shows 70% or higher, preferably 80% or higher, more preferably 90% or higher, and further preferably 95% or higher homology to the amino acid sequence as shown in SEQ ID NO: 2 and has D-LDH activity.

According to a further embodiment, the protein has an amino acid sequence derived from the amino acid sequence as shown in SEQ ID NO: 4 by substitution of one or more amino acid residues selected from the list of amino acid residue substitutions shown in Table 1 and has D-LDH activity. The amino acid sequence as shown in SEQ ID NO: 4 is the sequence of D-LDH of *Leuconostoc mesenteroides* registered with GenBank (GenBank Accession No. L29327). The amino acid sequence as shown in SEQ ID NO: 2 is derived from the amino acid sequence as shown in SEQ ID NO: 4 via all substitutions indicated in the list of amino acid residue substitutions shown in Table 1. Even if the amino acid sequence does not have all the substitutions, however, a protein having D-LDH activity that may be utilized in the present invention can be obtained. The number of substitutions is preferably 2 or more, more preferably 11 or more, and further preferably 19 or more.

The amino acid sequence preferably has amino acid substitutions indicated by substitution types 1 to 19, and more preferably those indicated by substitution types 6 to 16, in the list of amino acid residue substitutions shown in Table 1.

According to a further embodiment of the present invention, the protein comprises an amino acid sequence containing at least amino acid residues 78 and 79, 152 to 175, 235, and 296 of the amino acid sequence as shown in SEQ ID NO: 2 and has D-lactate dehydrogenase (D-LDH) activity. Amino acid residues 78 and 79, 152 to 175, 235, and 296 are considered to be characteristic of the amino acid sequence as shown in SEQ ID NO: 2. When a protein contains such amino acid sequence and has D-LDH activity, it can be said to be a preferable protein according to the present invention. More preferably, a protein has a histidine residue at position 296 as an active center and the coenzyme NADH binding domain constituted by amino acid residues 152 to 175 of the amino acid sequence as shown in SEQ ID NO: 2.

The protein of the present invention does not necessarily consist of the nucleotide sequence as shown in SEQ ID NO: 2, as long as it has D-LDH activity.

The protein of the present invention can be obtained by culturing the *Leuconostoc mesenteroides* strain IFO3426. Specifically, the protein can be obtained as a culture product thereof. Such strain can be cultured via a conventional bacterial culture technique. The protein of the present invention can be purified from the culture product in accordance with a conventional technique. Alternatively, a culture product itself or bacteria may be recovered and then used as the substance having enzyme activity of the present invention. Bacteria, purified enzymes, or crudely purified enzymes can be used as they are, or they may be immobilized.

The protein of the present invention can be obtained by adequately introducing mutation such as substitution, deletion, insertion, and/or addition into the amino acid sequence as shown in SEQ ID NO: 2 or another amino acid sequence via, for example, site-directed mutagenesis (Current Protocols in Molecular Biology, edited by Ausubel et al., Sections 8.1-8.5, 1987, John Wily & Sons). Such modification is not limited to artificial mutagenesis or synthesis. It also includes a product resulting from amino acid mutation in nature on the basis of artificial mutation, but it is not limited thereto.

Further, a polynucleotide consisting of the nucleotide sequence as shown in SEQ ID NO: 1 or DNA as a homolog thereof may be obtained, such DNA may be introduced into a host strain to prepare a transformant, and the resulting transformant may then be cultured. Thus, a homolog protein can be obtained.

In the present invention, for example, known proteins having D-LDH activity can be employed. Examples of proteins that can be employed include proteins derived from prokaryotic organisms such as *Lactobacillus, Escherichia coli, Bacillus subtilis*, or fungi or proteins derived from eukaryotic organisms such as yeast or octopus.

Such protein does not necessarily have the amino acid sequence as shown in SEQ ID NO: 2. It is not necessarily a homolog of the protein consisting of such amino acid sequence. The transformant of the present invention that carries a protein having D-LDH activity in an expressible manner is useful for producing D-LDH and D-lactic acid.

Cells that are preferable for obtaining the polynucleotide or protein of the present invention, the transformant of the present invention and that are gene resources of polynucleotides or proteins are not limited to naturally occurring organisms. Microorganisms or cells that were obtained via mutation or the like may be employed as gene resources.

The protein that is employed in the present invention has D-LDH activity. Such activity can be measured using, for example, a commercialized kit (lactate dehydrogenase (LDH/LD) test-UV (Sigma)).

(DNA Construct)

The isolated polynucleotide that encodes a protein having D-LDH activity (DNA, it may be hereinafter referred to as "D-LDH-DNA" when the polynucleotide is DNA) may be used to prepare a DNA construct having such DNA segment. This DNA construct can be used as an expression vector in such state or by being introduced into a suitable vector. A host cell is transformed using such DNA construct. Thus, a transformant that produces a protein having D-LDH activity can be obtained. Further, this transformant may be cultured to produce a protein having D-LDH activity. Also, D-lactic acid can be produced.

Transformation of a host cell involves the use of a DNA construct that allows expression of a DNA segment consisting of D-LDH-DNA in a host cell. Embodiments of a DNA construct for transformation are not particularly limited. In accordance with the form of the foreign gene introduced (extrachromosomal or intrachromosomal) or the type of host cell, plasmid (DNA), bacteriophage (DNA), retrotransposon (DNA), or an artificial chromosome (e.g., YAC, PAC, BAC, or MAC) can be selected. Accordingly, this DNA construct can comprise a constitutive segment of a vector according to any of the aforementioned embodiments in addition to the DNA of interest. Preferable prokaryotic vectors, eukaryotic vectors, animal cell vectors, and plant cell vectors are known in the art.

Examples of plasmid DNA include: YCp *Escherichia coli*-yeast shuttle vectors, such as pRS413, pRS415, pRS416, YCp50, pAUR112, or pAUR123; YEp *Escherichia coli*-yeast shuttle vectors, such as pYES32 or YEp13; YIp *Escherichia coli*-yeast shuttle vectors, such as pRS403, pRS404, pRS405, pRS406, pAUR101, or pAUR135; plasmids derived from *Escherichia coli* (e.g., ColE plasmids, such as pBR322, pBR325, pUC18, pUC19, pUC119, pTV118N, pTV119N, pBluescript, pHSG298, pHSG396, or pTrc99A; p1A plasmids, such as pACYC177 or pACYC184; or pSC101 plasmids, such as pMW118, pMW119, pMW218, or pMW219); and plasmids derived from *Bacillus subtilis*, such as pUB110 or pTP5. Examples of phage DNA include λ phage (e.g., Charon4A, Charon21A, EMBL3, EMBL4, λgt100, gt11, or zap), φX174, M13 mp18, and M13mp19. An example of retrotransposon is a Ty factor. An example of YAC is pYACC2.

The DNA construct of interest can be prepared by, for example, cleaving a fragment containing D-LDH-DNA with an adequate restriction enzyme and inserting the fragment into a restriction site or a multicloning site of the vector DNA to be used.

According to the first embodiment of the present invention, the DNA construct comprises a promoter segment to which a DNA segment consisting of D-LDH-DNA is ligated in an expressible manner. Specifically, this DNA segment is ligated to a site located downstream of the promoter, so that the promoter can control such DNA segment.

A protein having D-LDH activity is preferably expressed in yeast. Accordingly, use of a promoter that is capable of expressing such protein in yeast is preferable. Examples of a promoter that can be preferably used include a pyruvate decarboxylase gene promoter, a gall promoter, a gal10 promoter, a heat shock protein promoter, an MFα1 promoter, a PH05 promoter, a PGK promoter, a GAP promoter, an ADH promoter, and an AOX1 promoter. A promoter of the pyruvate decarboxylase 1 gene derived from *Saccharomyces* is particularly preferable, and use of the promoter of the pyruvate decarboxylase 1 gene derived from *Saccharomyces cerevisae* is more preferable. The expression of proteins induced by these promoters is enhanced in the ethanol fermentation pathway of *Saccharomyces* (*cerevisae*). The promoter sequence of interest can be isolated by PCR amplification wherein the genomic DNA of the pyruvate decarboxylase 1 gene of the yeast *Saccharomyces* is used as a template. For example, the nucleotide sequence of the promoter derived from *Saccharomyces cerevisae* is shown in SEQ ID NO: 5. The promoter segment in the DNA construct can be DNA consisting of the nucleotide sequence as shown in SEQ ID NO: 5, DNA consisting of a nucleotide sequence derived from the nucleotide sequence as shown in SEQ ID NO: 5 by deletion, substitution, insertion, and/or addition of one or several nucleotides and having promoter activity, or DNA that can hybridize under stringent conditions with DNA comprising all or part of the nucleotide sequence as shown in SEQ JD NO: 5 or a complementary strand thereof and having promoter activity (i.e., a homolog of such promoter). Also, promoters of the pyruvate decarboxylase gene or the pyruvate decarboxylase 1 gene derived from other types of yeast or other types of the yeast *Saccharomyces cerevisae* can also be used.

According to the second embodiment of the present invention, the DNA construct comprises a DNA segment for homologous recombination of a host chromosome in addition to DNA. The DNA segment for homologous recombination has a DNA sequence that is homologous to the DNA sequence in the vicinity of the target site in a host chromosome into which the DNA of interest is to be introduced. The DNA construct comprises at least 1, and preferably 2, DNA segments for homologous recombination. For example, DNA sequences homologous to DNA located at sites upstream and downstream of the target site on the chromosome are provided as 2 DNA segments for homologous recombination, and the DNA of interest is preferably ligated to a site between these DNA segments.

When the DNA of interest is introduced into a host chromosome via homologous recombination, such DNA can be introduced in a manner such that the promoter on the host chromosome is able to control the DNA. In such a case, introduction of the target gene can also disrupt the endogenous gene that should be controlled by the promoter and can allow expression of foreign D-LDH-DNA instead of the endogenous gene. It is particularly useful when such promoter is capable of enhanced expression in a host cell.

In order to create such expression system on a host chromosome, genes capable of enhanced expression are targeted in the host chromosome, and D-LDH-DNA is preferably introduced into a site downstream of the promoter that controls the gene of interest in a manner such that the D-LDH-DNA can be controlled by such promoter. When an ethanol fermentation microorganism such as yeast is used as a host, the pyruvate decarboxylase gene (particularly the pyruvate decarboxylase 1 gene) is targeted, and DNA that encodes a protein having LDH activity can be introduced under the control of the promoter of the endogenous pyruvate decarboxylase gene. In such a case, a DNA segment for homologous recombination can be homologous to a sequence in the LDH structural gene domain of the pyruvate decarboxylase 1 gene or a sequence in the vicinity thereof (including a sequence in the vicinity of the initiation codon, a sequence upstream of the initiation codon, a sequence in the structural gene, and the like). A segment of the promoter of the pyruvate decarboxylase gene can be included in the DNA construct.

Preferably, the yeast *Saccharomyces* (particularly *Saccharomyces cerevisae*) is used as a host, and a DNA construct that targets the pyruvate decarboxylase 1 gene of this host is prepared. Such DNA construct can disrupt the pyruvate decarboxylase 1 gene and substitute this structural gene portion with D-LDH by using a single vector. Pyruvate decarboxylase 1 is an enzyme that mediates the irreversible reaction from pyruvic acid to acetaldehyde. Disruption of the gene thereof can inhibit the conversion of pyruvic acid to acetaldehyde and then to ethanol. Also, generation of D-lactic acid by D-LDH can be accelerated with the use of pyruvic acid as a substrate.

The DNA construct according to the first embodiment can also be a DNA construct for homologous recombination by comprising a DNA segment for homologous recombination with a host chromosome. In the case of the DNA construct according to the first embodiment, a promoter segment thereof can also serve as a DNA segment for homologous recombination with a host chromosome. For example, a DNA construct that has a promoter of a *Saccharomyces cerevisae* host chromosome, such as a promoter of the pyruvate decarboxylase 1 gene as a promoter segment, constitutes a targeting vector having the gene of the host as a target site. In such a case, a DNA construct preferably comprises a sequence homologous to the sequence of the structural gene domain located downstream of the pyruvate decarboxylase 1 gene.

According to need, a cis element such as an enhancer, a splicing signal, a poly A addition signal, a selection marker, or a ribosome binding sequence (SD sequence) can be ligated to the DNA construct, in addition to a terminator. A selection marker is not particularly limited, and various conventional selection marker genes, including drug-resistant genes and auxotrophic genes, can be used. For example, the dihydrofolate reductase gene, the hygromycin B gene, and the neomycine resistant gene can be used.

(Transformation Using DNA Construct)

Once a DNA construct is prepared, such DNA construct can be introduced into an adequate host cell via any adequate techniques such as transformation, transfection, conjugation, protoplast fusion, electroporation, lipofection, the lithium acetate method, the particle gun method, calcium phosphate precipitation, the agrobacterium method, the PEG method, or direct microinjection. After the DNA construct has been introduced, the recipient cell is then cultured in a selection medium.

Examples of host cells include: bacteria such as *Escherichia coli* and *Bacillus subtilis*; yeast such as *Saccharomyces cerevisae, Schizosaccharomydces pombe,* and *Pichia pastoris*; insect cells such as sf9 and sf21; animal cells such as COS cells and Chinese hamster ovary (CHO) cells; and plant cells such as sweet potato and tobacco. Preferably, host cells are alcohol fermentation microorganisms or acid resistant microorganisms such as yeasts. Examples thereof include the yeast *Saccharomyces*, such as *Saccharomyces cerevisae*. Specific examples thereof include the *Saccharomyces cerevisae* strains IFO2260 and YPH.

The transformant prepared from the DNA construct of interest comprises a constituent of such DNA construct in the chromosome or extrachromosomal element (including an artificial chromosome). When the DNA construct is maintained extrachromosomally or integrated into a chromosome via random integration, genes of another type of enzymes that act on the pyruvic acid as a substrate, which is also a substrate of LDH, such as the pyruvate decarboxylase gene (and the pyruvate decarboxylase 1 gene in the case of the yeast *Saccharomyces cerevisae*) are preferably knockout via a targeting vector If the aforementioned DNA construct capable of homologous recombination is introduced, a ligated D-LDH-DNA is located at a site downstream of a desired promoter or the promoter substituted by the desired promoter or a homolog thereof in a manner such that such promoter can control D-LDH-DNA. A transformant of the yeast *Saccharomyces* preferably comprises on the host chromosome D-LDH-DNA at a site downstream of the promoter of the pyruvate decarboxylase 1 gene or the promoter substituted by the promoter or a homolog in a manner such that such promoter can control D-LDH-DNA. In general, a homologous recombinant comprises a selection marker gene or a part of the disrupted structural gene (a site corresponding to a homologous sequence on the DNA construct) in its site downstream of D-LDH-DNA.

As a result of introduction of the DNA construct, a protein encoded by D-LDH-DNA is generated. Upon disruption of the pyruvate decarboxylase gene of yeast, D-LDH is introduced under the control of the promoter of the gene or a homolog thereof. This can result in the production of D-LDH in a type of yeast that does not originally produce D-lactic acid, which in turn results in the production of D-lactic acid.

More particularly, introduction of D-LDH-DNA into a site downstream of the promoter of the pyruvate decarboxylase 1 gene of yeast (specifically, Saccharomyces, and typically Saccharomyces cerevisae) or a homolog thereof can result in selective production of D-lactic acid. It is deduced that if D-LDH-DNA encodes a protein having D-LDH activity, the expression of D-LDH is enhanced with the aid of such promoter, which also positively affects the enhanced production of D-lactic acid. In contrast, D-LDH-DNA encodes a protein consisting of the amino acid sequence as shown in SEQ ID NO: 2. This is deduced to result in the enhanced and/or selective production of D-lactic acid.

Whether or not D-LDH-DNA has been introduced into a site downstream of a desired promoter can be confirmed via PCR, Southern hybridization, or other means. For example, DNA may be prepared from a transformant, such DNA may be subjected to PCR using a primer for site-directed mutagenesis, and the PCR product may be then subjected to electrophoresis to detect an expected band. Alternatively, confirmation can be made via PCR using a primer labeled with a fluorescent dye or the like. Confirmation can also be made based on the protein produced by the transformant. These techniques are known in the art.

It is preferable to prepare a transformant into which multicopy D-LDH genes have been introduced via introduction of a DNA construct. When a yeast transformant is prepared, for example, at least 2 copies and preferably 4 to 10 copies of D-LDH-DNAs are introduced. A transformant into which multicopy D-LDH genes have been introduced has significantly improved capacity for D-lactic acid production. That is, the use of a transformant into which multicopy D-LDH genes have been introduced can result in significantly improved D-lactic acid productivity.

(Production of D-lactic Acid)

Culturing of the transformant into which the DNA construct of the present invention has been introduced leads to the generation of D-LDH, which is the expression product of a foreign gene, in the culture product. It further leads to the generation of D-lactic acid. Lactic acid can be obtained by performing a step of separating lactic acid from the culture product. In the present invention, examples of the culture product include a cultured cell or bacterium and a disrupted cell or bacterium in addition to the culture supernatant.

In the present invention, D-lactic acid can be selectively produced using, for example, a type of yeast cell that does not originally produce D-lactic acid as a host. Use of fermentation microorganisms is particularly effective for obtaining D-lactic acid. A transformant resulting from a yeast host is effective for enhanced production of D-lactic acid because of its fast growth rate. With the use of such transformant having the capacity for selective production of D-lactic acid, the need for separating an optical isomer is eliminated, which in turn results in more effective production of D-lactic acid.

The transformant of the present invention can be cultured under adequate conditions in accordance with the type of transformant. Such adequate conditions are known in the art.

As a medium for culturing the transformant obtained from a microorganism host such as E. coli or yeast, either a natural or synthetic medium may be used as long as it contains carbon sources, nitrogen sources, and inorganic salts assimilable by the microorganism and is capable of efficiently culturing the transformant. Examples of carbon sources include: carbohydrates such as glucose, fructose, sucrose, starch, and cellulose; organic acids such as acetic acid and propionic acid; and alcohols such as ethanol and propanol. Examples of nitrogen sources include: ammonia; ammonium salts of inorganic or organic acids such as ammonium chloride, ammonium sulfate, ammonium acetate, and ammonium phosphate; other nitrogen-containing compounds; peptone; meat extract; and corn steep liquor. Examples of inorganic substances include: monopotassium phosphate, magnesium phosphate, magnesium sulfate, sodium chloride, iron(I) sulfate, manganese sulfate, copper sulfate, and calcium carbonate.

Usually, culture is carried out under aerobic conditions, such as shake culture or aeration agitation culture, at 30° C. for an adequate period of time. For example, culture can be carried out for 6 to 120 hours. During the culture, the pH is preferably maintained at 2.0 to 6.0. The pH can be adjusted with an inorganic or organic acid, an alkali solution, or the like.

Examples of media for culturing a transformant obtained from an animal host cell include common RPMI 1640 medium, DMEM medium, and a medium prepared by adding fetal bovine serum or the like to the aforementioned medium. Usually, culture is carried out in the presence of 5% $CO_2$ at 37° C. for 1 to 30 days. During the culture, an antibiotic such as kanamycin or penicillin may be added to the medium, if necessary.

Culture may be carried out via a batch or continuous system. Culture may be carried out by a method wherein the transformant is subjected to neutralization with an alkali such as ammonium or calcium salt to obtain lactates such as ammonium-D-lactate or calcium D-lactate. Alternatively, a culture product may be free D-lactic acid.

After the completion of the culture, D-lactic acid, which is the gene product, can be separated from the culture product via suitable combinations of common purification techniques and the like. When D-lactic acid is produced in transformed cells, for example, cells are disrupted via conventional techniques such as ultrasonic disintegration, grinding, or pressure disruption to separate the gene product from such cells. In such a case, protease is added according to need. When D-lactic acid is produced in the culture supernatant, this solution is subjected to filtration, centrifugation, or other means to remove solid components.

After the completion of the step of culturing, for example, a culture solution can be subjected to a step of solid-liquid separation via at least one of belt press, centrifugation, or filter press. The separated filtrate is preferably subjected to a step of purification. In the step of purification, for example, a lactic acid-containing filtrate can be subjected to electrodialysis to remove organic acids other than lactic acid and saccharides. Thus, an aqueous solution of lactic acid or ammonium lactate can be prepared. In the case of an ammonium lactate solution, ammonia is degraded via a bipolar membrane or the like to separate an aqueous solution of lactic acid from aqueous ammonia. When the content of organic acids other than lactic acid or that of saccharides in the filtrate is relatively small, electrodialysis is not to be performed. In such a case, the filtrate may be concentrated by vaporizing its moisture content according to need, and ammonia can be degraded via a bipolar membrane.

The temperature of a solution at the time of electrodialysis is generally in the range of 20° C. to 45° C. and preferably in the range of 35° C. to 40° C. Amino acids, inorganic ions (e.g., K, Ca, or Mg), and organic acids (e.g., citric acid or malic acid) that were not removed via electrodialysis can be removed with the use of a chromatographic separator or ion exchanger at a later stage. Further, the resulting lactic acid solution can be concentrated, if necessary. For example, moisture in the solution can be evaporated to obtain a 50% to 90% lactic acid solution.

Techniques for separating and purifying D-lactic acid or a salt thereof from the culture solution or the crude extract are not limited to the aforementioned. A variety of purification and separation techniques, such as separation and extraction or distillation with the use of an organic solvent, can be employed to separate and purify D-lactic acid or a salt thereof. If necessary, the culture solution, the crude extract, and a purified product thereof can be subjected to esterification, lactide conversion, oligomerization, prepolymerization, or the like. Thus, various D-lactic acid derivatives can be obtained. According to need, one or more of D-lactic acid, a salt thereof, and a derivative thereof can be recovered from a solution of fermented lactic acid.

D-lactic acid can also be produced via an enzyme reaction system instead of a culture system with the use of the protein having D-LDH activity of the present invention. D-lactic acid can be produced under any enzyme reaction conditions as long as they allow D-lactic acid to be produced. A variety of induction techniques can be applied to D-lactic acid obtained by such techniques.

(Production of Lactic Acid Polymer)

The obtained D-lactic acid, a salt thereof, and a derivative thereof can be used as at least one type of polymerization material to produce a lactic acid polymer. Examples of polymerization materials that can be used include monomers such as D-lactic acid or derivatives thereof and prepolymers or oligomers resulting from polymerization of such monomers to adequate lengths. Further, L-lactic acid or derivatives thereof and prepolymers or oligomers thereof can also be used.

Examples of lactic acid polymers include homopolymers of D-lactic acids, heteropolymers of D-lactic acid and L-lactic acid, hetero-block polymers, and various types of heteropolymers of lactic acids and other polymerization materials.

These lactic acid polymerization materials, or a lactic acid polymerization material and another polymerization material, may be allowed to react with an adequate polymerization initiator to produce lactic acid polymers.

According to the present invention, selective and/or enhanced production of D-lactic acid is possible. Thus, D-lactic acid can be effectively obtained, which results in effective production of lactic acid polymers that comprise D-lactic acid as a polymerization material.

EXAMPLES

Hereafter, the examples of the present invention are described, although the present invention is not limited thereto. A variety of modification can be made within the scope of the present invention.

Example 1

Isolation of D-lactate Dehydrogenase Gene

The D-lactate dehydrogenase genes derived from prokaryotic lactic acid bacteria, *Leuconostoc mesenteroides* (D-LDH genes, hereafter they may be simply referred to as "D-LDHME genes"), were isolated.

The genomic DNA of the strain IFO3426 (registered with the Institute for Fermentation) was used as a template to isolate the gene resource via PCR amplification. The genomic DNA of this strain was prepared using a genome DNA preparation kit (Fast DNA Kit, Bio 101) in accordance with the protocol included with the kit. The prepared genomic DNA was subjected to DNA concentration measurement using the Ultrospec 3000 spectrophotometer (Amersham Pharmacia Biotech).

The KOD Plus DNA Polymerase (Toyobo Co., Ltd.), which is perceived as having high accuracy, was used as the amplification enzyme in PCR. The reaction solution (50 µl in total) comprising 50 ng of the previously prepared genomic DNA, 50 pmol of ×2 primer DNA, 5 µl of 10× buffer for KOD enzyme reaction, 2 µl of 25 mM $MgSO_4$, 5 µl of 2 mM dNTP mix, and 1.0 unit of KOD plus DNA polymerase was subjected to DNA amplification using a PCR amplification apparatus (GeneAmp PCR system 9700, PE Applied Biosystems).

PCR was carried out under the following conditions. Heat treatment was first carried out at 96° C. for 2 minutes, followed by a 3-stage temperature change cycle of 96° C. for 30 seconds, 53° C. for 30 seconds, and 72° C. for 90 seconds. This cycle was repeated 25 times, and the temperature was reduced to 4° C. at the end. The reaction sample (5 µl) was electrophoresed on 1% TBE agarose gel (containing 0.5 µg/ml ethidium bromide), and DNA bands were detected by irradiating the gel with ultraviolet rays of 254 nm (Funakoshi) to confirm the amplified gene fragment.

The synthetic DNA primers (Sawady Technology) were used for the reaction, and the DNA sequences of these primers are as shown below.

```
DLDEME-U (21mer, Tm value of 57.2° C.)
                                 (SEQ ID NO: 6)
5'-ATG AAG ATT TTT GCT TAC GGC-3'

DLDEME-U (24mer, Tm value of 54.7° C.)
                                 (SEQ ID NO: 7)
5'-ATC TTA ATA TTC AAC AGC AAT AGC-3'
```

The PCR-amplified fragment was subcloned into the pBluescriptII SK+ vector (Toyobo Co., Ltd.). The reaction was carried out in accordance with a general technique for DNA subcloning. Specifically, the amplified gene fragment obtained in Example 1 was ligated to the aforementioned vector, which was processed with the EcoRV restriction enzyme (Takara Shuzo Co., Ltd.) and the Alkaline Phosphatase dephosphorylation enzyme (Takara Shuzo Co., Ltd.), using T4 DNA ligase. The reaction using T4 DNA ligase was carried out using LigaFast Rapid DNA Ligation (Promega) in accordance with the protocol included therewith.

Subsequently, the ligation reaction solution was transformed into *E. coli* competent cells. JM109 competent *E. coli* cells (Toyobo Co., Ltd.) were used, and transformation was carried out in accordance with the protocol included therewith. Colony selection was carried out on an LB plate that contains 100 µg/ml ampicillin, plasmid DNA was prepared from each selected colony, and the plasmid DNA was subjected to PCR using the aforementioned primer DNA to subclone the D-LDH gene of interest. Ethanol precipitation, restriction enzyme treatment, and the like were carried out in accordance with the instructions described in Molecular Cloning: A Laboratory Manual, 2nd Ed., Maniatis et al., Cold Spring Harbor Laboratory Press, 1989.

The nucleotide sequence of the D-LDH gene thus obtained was determined. The ABI PRISM 310 Genetic Analyzer (PE Applied Biosystems) was used as an apparatus for nucleotide sequence analysis, and the method for sample preparation, the use of apparatus, and other conditions were determined in accordance with the instructions included with the apparatus. The vector DNA containing the isolated D-LDH gene was prepared by the alkaline extraction method, then the vector DNA was subjected to column purification using the GFX DNA Purification kit (Amersham Pharmacia Biotech), followed by the DNA concentration was measured using the Ultrospec 3000 spectrophotometer (Amersham Pharmacia Biotech), and the vector DNA, the concentration of which had been adjusted, was used.

The DNA sequence determined via sequence analysis is shown in SEQ ID NO: 1, and the corresponding amino acid sequence is shown in SEQ ID NO: 2.

The nucleotide sequence of the D-LDHME gene isolated in the present example was compared with the sequence of the D-LDH gene that has been already registered with GenBank (GenBank Accession No. L29327, derived from the lactic acid bacteria *Leuconostoc mesenteroides*, SEQ ID NO: 3). This revealed that these sequences were different from each other in terms of 19 amino acid residues at the amino acid sequence level and in terms of 27-bp nucleotides at the nucleotide sequence level.

FIG. 1A and FIG. 1B show the homology data of the nucleotide sequence (SEQ ID NO: 1) of the D-LDHME gene that was obtained in the present example and the nucleotide sequence (SEQ ID NO: 3) of the D-LDH gene that has been registered with GenBank. The upper sequence shows the nucleotide sequence of the D-LDHME gene that was obtained in the present example, and the lower sequence shows the nucleotide sequence of the D-LDH gene that has been registered with GenBank.

FIG. 2 shows the homology data of the amino acid sequence (SEQ ID NO: 2) corresponding to the nucleotide sequence of the D-LDHME gene that is obtained in the present example and the amino acid sequence (SEQ ID NO: 4) corresponding to the nucleotide sequence of the D-LDH gene that has been registered with GenBank. The upper sequence shows the amino acid sequence corresponding to the D-LDHME gene that was obtained in the present example, and the lower sequence shows the amino acid sequence corresponding to the D-LDH gene that has been registered with GenBank.

Based on the amino acid sequences, the amino acid sequences of the genes obtained in the present example were found to have amino acid residue substitutions as shown in Table 2.

TABLE 2

| List of amino acid residue substitutions | | |
| --- | --- | --- |
| Substitution type | Position of substitution | Amino acid substituent |
| 1 | 40 | Valine (Val) |
| 2 | 112 | Isoleucine (Ile) |
| 3 | 131 | Histidine (His) |
| 4 | 139 | Isoleucine (Ile) |
| 5 | 181 | Glutamic acid (Glu) |
| 6 | 266 | Glycine (Gly) |
| 7 | 267 | Leucine (Leu) |
| 8 | 268 | Phenylalanine (Phe) |
| 9 | 269 | Asparagine (Asn) |
| 10 | 270 | Glutamic acid (Glu) |
| 11 | 271 | Aspartic acid (Asp) |
| 12 | 272 | Tryptophan (Trp) |
| 13 | 273 | Serine (Ser) |
| 14 | 274 | Glycine (Gly) |
| 15 | 276 | Glutamic acid (Glu) |
| 16 | 277 | Phenylalanine (Phe) |
| 17 | 287 | Serine (Ser) |
| 18 | 292 | Leucine (Leu) |
| 19 | 293 | Valine (Val) |

In this table, positions of substitution are indicated as the positions from methionine, which corresponds to the initiation codon.

Example 2

Construction of Recombinant Vector

A chromosomally integrated vector capable of expressing a target gene, i.e., the D-LDHME gene obtained in Example 1, was constructed. This vector is capable of expressing the target gene under the control of the promoter sequence of the pyruvate decarboxylase 1 gene (PDC1) derived from *Saccharomyces cerevisae*. Such newly constructed and chromosomally integrated vector was designated as the pBTRP-PDC1-DLDHME vector. Construction of the vector was carried out in accordance with the general technique for DNA subcloning.

Hereafter, the process of vector construction in the present example is described in detail with reference to FIGS. 3 to 6.

All the enzymes used for vector construction were manufactured by Takara Shuzo Co., Ltd. It should be noted that the possible vector construction processes are not limited to this process.

1. Isolation of a Promoter Fragment of the PDC1 Gene (PDC1P) and a Downstream Fragment of the PDC1 Gene (PDC1D)

The 971-bp promoter fragment of the PDC 1 gene (PDC1P) and the 518-bp downstream fragment of the PDC1 gene (PDC1D), which were essential for vector construction, were isolated from the gene resource, i.e., the *Saccharomyces cerevisae* strain IFO2260, via PCR amplification that used the genomic DNA of this strain as a template. The strain IFO2260 is registered with the Institute for Fermentation. The genomic DNA of this strain was prepared using a genome DNA preparation kit (Fast DNA Kit, Bio 101) in accordance with the protocol included with the kit. The prepared genomic DNA was subjected to DNA concentration measurement using the Ultrospec 3000 spectrophotometer (Amersham Pharmacia Biotech).

The KOD Plus DNA Polymerase (Toyobo Co., Ltd.), which is perceived as having high accuracy, was used as the amplification enzyme in PCR. The reaction solution (50 μl in total) comprising 50 ng of the previously prepared genomic DNA of the strain IFO2260, 50 μmol of primer DNA×2, 5 μl of 10× buffer for KOD enzyme reaction, 2 μl of 25 mM MgSO$_4$, 5 μl of 2 mM dNTP mix, and 1.0 unit of KOD plus DNA polymerase was subjected to DNA amplification using a PCR amplification apparatus (Gene Amp PCR system 9700, PE Applied Biosystems).

PCR was carried out under the following conditions. Heat treatment was first carried out at 96° C. for 2 minutes, followed by a 3-stage temperature change cycle of 96° C. for 30 seconds, 53° C. for 30 seconds, and 72° C. for 90 seconds. This cycle was repeated 25 times, and the temperature was reduced to 4° C. at the end. The reaction sample (5 µl) was electrophoresed on 1% TBE agarose gel (containing 0.5 µg/ml ethidium bromide), and DNA bands were detected by irradiating the gel with ultraviolet rays of 254 nm (Funakoshi) to confirm the amplified gene fragment.

The synthetic DNA primers (Sawady Technology) were used for the reaction, and the DNA sequences of these primers are as shown below.

[Primers for PDC1P Fragment Amplification]
PDC1P-LDH-U (31mer, Tm value of 58.3° C.)

(SEQ ID NO: 8)
5'-ATA TAT GGA TCC GCG TTT ATT TAC CTA TCT C-3'

(underlined portion: BamHI site)
PDCIP-LDH-D (31mer, Tm value of 54.4° C.)

(SEQ ID NO: 9)
5'-ATA TAT GAA TTC TTT GAT TGA TTT GAC TGT G-3'

(underlined portion: EcoRI site)
[Primers for PDC1D Fragment Amplification]
PDC1D-LDH-U (31mer, Tm value of 55.3° C.)

(SEQ ID NO: 10)
5'-ATA TAT CTC GAG GCC AGC TAA CTT CTT GGT CGA C-3'

(underlined portion: XhoI site)
PDC1D-LDH-D (31mer, Tm value of 65.2° C.)

(SEQ ID NO: 11)
5'-ATA TAT GGG CCC CCC CTC GAG GTC CCC CCT C-3'

(underlined portion: ApaI site)

The amplified fragments of the PDC1P and PDC1D genes obtained in the above reaction were purified via ethanol precipitation, and the amplified PDC1P fragment and the amplified PDC1D fragment were cleaved with the BamHI and EcoRI restriction enzymes and the XhoI and ApaI restriction enzymes, respectively. Ethanol precipitation and restriction enzyme cleavage were carried out in accordance with the instructions described in Molecular Cloning: A Laboratory Manual, 2nd ed., Maniatis et al., Cold Spring Harbor Laboratory Press, 1989.

2. Construction of pBPDC1P Vector

The PDC1P fragment, which was amplified by PCR and cleaved with restriction enzymes, was ligated to the pBluescriptII SK+ vector (Toyobo Co., Ltd.), which was processed with the restriction enzymes BamHI and EcoRI (Takara Shuzo Co., Ltd.) and the Alkaline Phosphatase dephosphorylation (BAP) enzyme (Takara Shuzo Co., Ltd.), using T4 DNA ligase (FIG. 3, upper portion). The reaction using T4 DNA ligase was carried out using LigaFast Rapid DNA Ligation (Promega) in accordance with the protocol included therewith.

Subsequently, the ligation reaction solution was transformed into E. Coli competent cells. JM109 competent cells (Toyobo Co., Ltd.) were used, and transformation was carried out in accordance with the protocol included therewith. The resulting culture solution was sowed on an LB plate containing 100 Hg/ml of antibiotic ampicillin, and culture was conducted overnight. The grown colony was subjected to colony PCR using primer DNA, and the prepared plasmid DNA solution via miniprep method was subjected to restriction enzyme processing to confirm the inserted fragment and then the target pBPDC1P vector was isolated (FIG. 3, middle portion).

3. Construction of pBPDC1P-LDHI Vector

As shown in FIG. 3, a fragment of the LDH gene (derived from Bifidobacterium longum) that can be obtained by treating the pYLD1 vector constructed by Toyota Motor Corporation (JP Patent Publication (Kokai) No. 2001-204468 (A)) with the EcoRI and AatII restriction enzymes and the end-modification enzyme, i.e., T4 DNA polymerase, was subcloned into the pBPDC1P vector that has been similarly processed with the EcoRI restriction enzyme and the end-modification enzyme, i.e., T4 DNA polymerase, in the manner as described above. Thus, the pBPDC1P-LDHI vector was prepared (FIG. 3, middle to lower portions). The aforementioned pYLD1 vector was introduced into E. coli (name: "E. coli pYLD1") and deposited internationally under the Budapest Treaty at the International Patent Organism Depositary of the National Institute of Advanced Industrial Science and Technology (Tsukuba Central 6, 1-1-1 Higashi, Tsukuba, Ibaraki, 305-8566, Japan) as of Oct. 26, 1999, under the accession number: FERM BP-7423 (the original deposit).

4. Construction of pBPDC1P-LDH Vector

Figure 4:
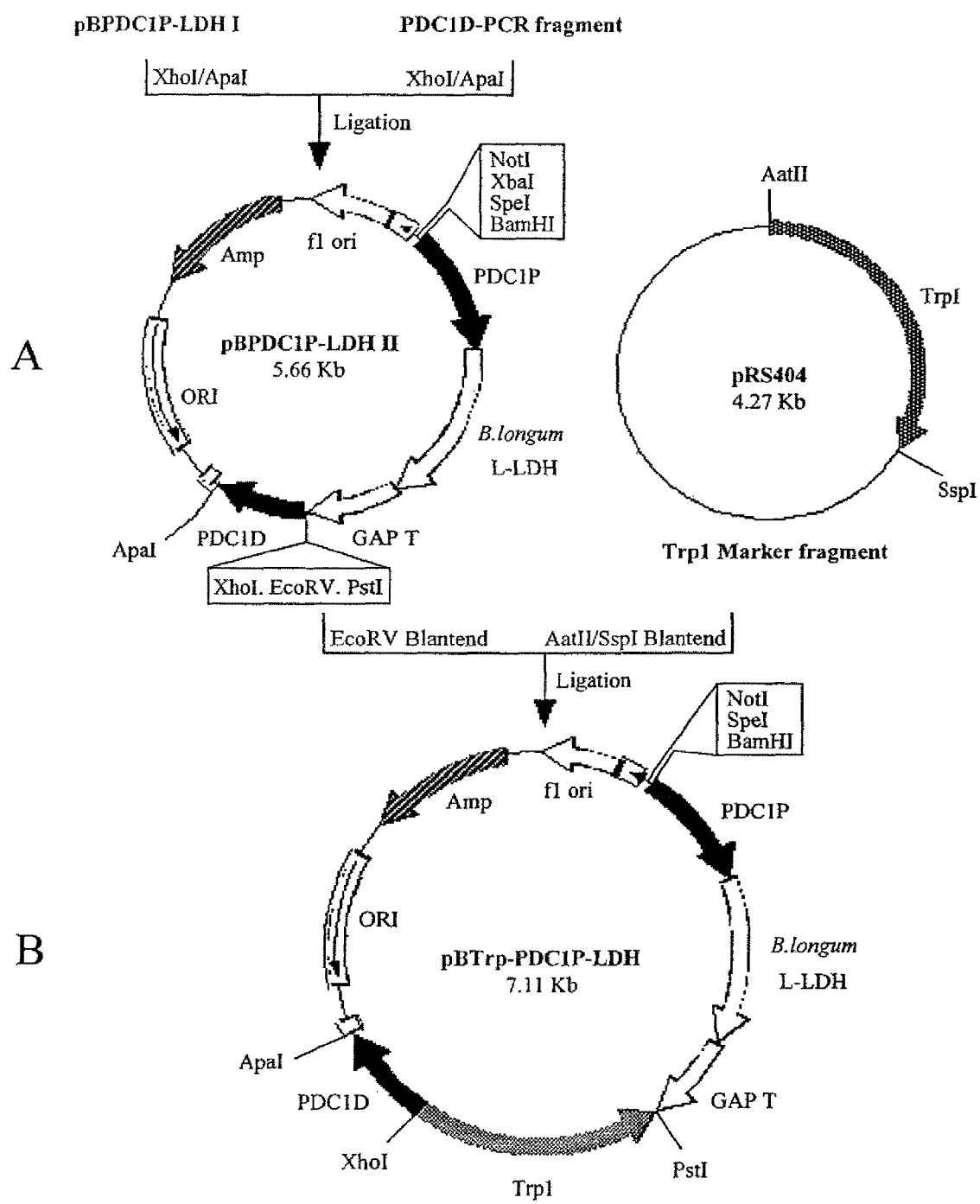
FIG. 4 shows a part of a procedure for constructing a pBTRP-PDC1-DLDHME vector.

As shown in FIG. 4, this vector was processed with the XhoI and ApaI restriction enzymes, and the amplified PDC1D fragment, which had been similarly processed with restriction enzymes, was ligated thereto to prepare the pBPDC1P-LDHII vector (FIG. 4, upper portion).

Subsequently, the pBPDC1P-LDHII vector was processed with EcoRV and T4 DNA polymerase, and the Trp marker fragment, which was obtained by processing the pRS404 vector (Promega) with AatII and SspI and T4 DNA polymerase, was ligated thereto to prepare the pBTRP-PDC1-LDH vector (FIG. 4, lower portion).

5. Construction of pBTRP-PDC1PII Vector

Figure 5:
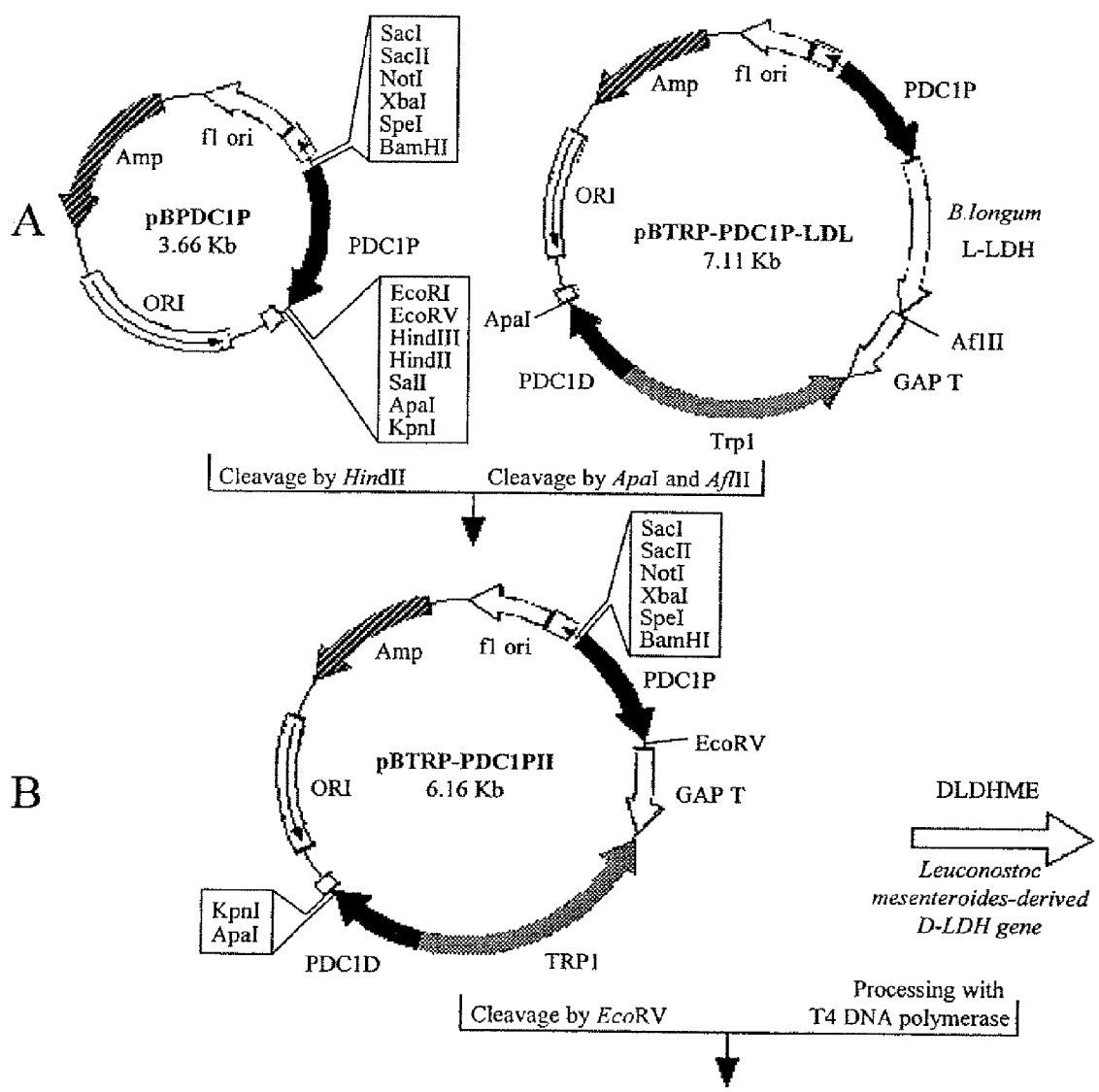
FIG. 5 shows a part of a procedure for constructing a pBTRP-PDC1-DLDHME vector.

As shown in FIG. 5, the existing pBPDC1P vector was processed with the HincII restriction enzyme and the Alkaline Phosphatase dephosphorylation enzyme. The pBTrp-PDC1-LDH vector was processed with the ApaI and AflII restriction enzymes and then with the end-modification enzyme, i.e., T4 DNA polymerase, to produce a fragment containing trp marker. This fragment was ligated to the processed pBPDC1P vector to construct the pBTRP-PDC1PII vector.

6. Construction of pBTRP-PDC1-DLDHME Vector

Figure 6:
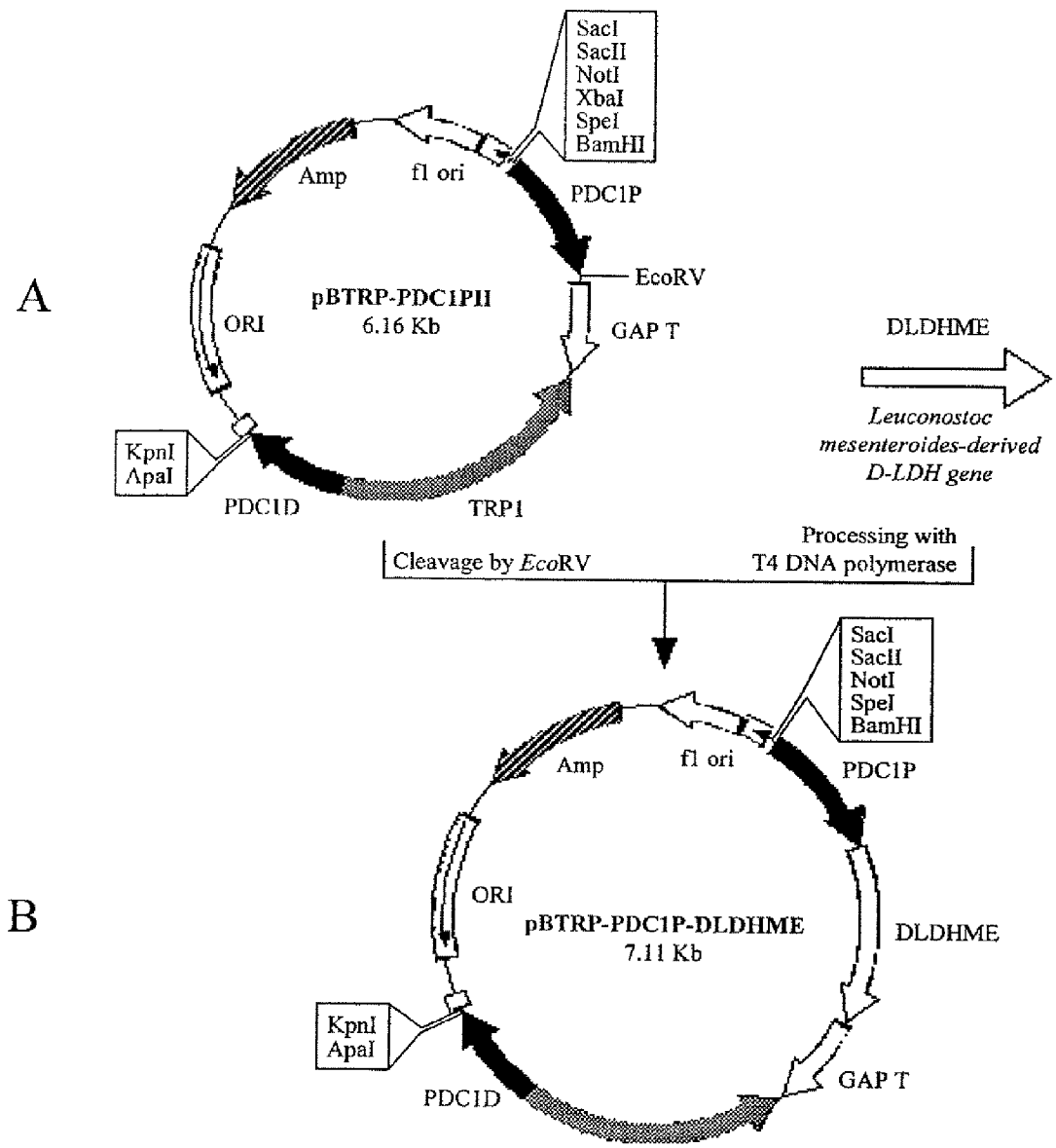
FIG. 6 shows the final step of a procedure for constructing a pBTRP-PDC1-DLDHME vector.

As shown in FIG. 6, the pBTRP-PDC1PII vector was processed with the EcoRV restriction enzyme and then with the end-modification enzyme, i.e., T4 DNA polymerase, and the fragment of the D-LDHME gene isolated in Example 1 was ligated thereto to construct the final vector, i.e., the chromosomally integrated pBTRP-PDC1-DLDHME vector.

As other D-LDH genes, oligonucleotides were synthesized in accordance with the gene sequence (SEQ ID NO: 3) of the GenBank Accession No. L29327 in the database of the D-LDH genes derived from lactic acid bacteria Leuconostoc mesenteroides. These oligonucleotides were successively ligated to fully synthesize the target D-LDH genes. The resulting gene fragments were subjected to the same procedures as those in the present example to construct a chromosomally integrated vector.

Example 3

Transformation of Yeast

The yeast host strain IFO2260 (registered with the Institute for Fermentation) lacking the capacity for tryptophan synthesis was cultured in 10 ml of YPD medium at 30° C. until the logarithmic growth phase, and cells were collected and washed with TE buffer. Subsequently, 0.5 ml of TE buffer and 0.5 ml of 0.2 M lithium acetate were added, the resultant was subjected to shake culture at 30° C. for 1 hour, and pBTRP-PDC1-DLDHME that had been processed with the ApaI and SpeI restriction enzymes (Takara Shuzo Co., Ltd.) was then added.

The resulting suspension was subjected to shake culture at 30° C. for 30 minutes, 150 µl of 70% polyethylene glycol 4000 (Wako Pure Chemical Industries, Ltd.) was added thereto, and the mixture was thoroughly stirred. The resultant was further subjected to shake culture at 30° C. for 1 hour, the culture product was treated with a heat shock of 42° C. for 5 minutes, and the cells were then cultured in 1 ml of YPD culture medium at 30° C. for 12 hours. The culture solution was washed and then suspended in 200 µl of sterilized water. The resulting suspension was then smeared on a tryptophan selection medium.

The resulting colony was isolated again in a new tryptophan selection medium, and strains that maintained the capacity for tryptophan synthesis were selected as candidate transformants. These strains were cultured in an YPD culture solution and genomic DNA thereof was prepared using a genome DNA preparation kit (Fast DNA Kit, Bio 101). The genomic DNA was subjected to PCR to confirm the presence or absence of the transgenes. As a result, strains having the D-LDHME genes introduced downstream of the PDC 1 promoter were found.

Figure 7:
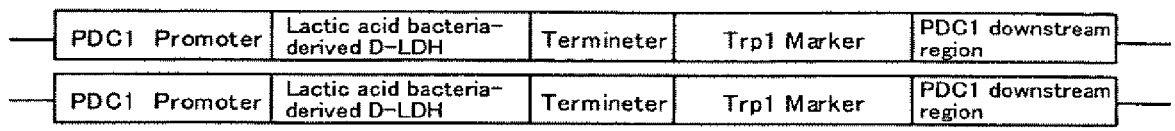
FIG. 7 shows a part of the chromosome structure of a diploid transformed yeast strain obtained in Example 3.

The obtained strains into which transgenes had been introduced were smeared on a sporulation-inducing medium, and sporulation was induced at 30° C. for 4 days. Cells were collected from the medium, 5 units of Zymolyase (Zymo Research Corp.) were added thereto, the resultant was subjected to enzyme reaction at 37° C. for 1 hour, and spores were then separated on YPD medium using a microscope (Olympus Corporation) and a micromanipulator (Narishige Scientific Instrument Laboratory). The progeny strains of the obtained spores were inspected for the capacity for tryptophan marker selection, and PCR was carried out to confirm that they showed 2:2 segregation. Thus, the target diploid strains were obtained. Diploid strains were the TC14-6-1A, TC14-6-2A, and TC14-6-3A strains. The obtained diploid strains had the structures shown in FIG. 7 in the yeast chromosomes.

Concerning the chromosomally integrated vector of other D-LDH genes constructed in Example 2, gene introduction into the strain IFO2260 lacking the capacity for tryptophan synthesis was similarly carried out, and the TC20-1-1A strains having chromosomally integrated D-LDH were found via PCR.

As the control, DLDHME was introduced into the pYPD1 plasmid, which is a yeast self-replicating 2µ plasmid vector, to construct a self-replicating vector. The resulting vector was similarly introduced into the strain IFO2260, and the strain TC21-1 was found to have plasmids containing D-LDH genes via PCR.

Example 4

Confirmation of Production of D-lactic Acid in a Transformant

The 5 types of transformants prepared in Example 3 and the parent strain IFO2260 were subjected to the fermentation test. These strains were inoculated into 5 ml of YPD liquid medium, subjected to shake culture at 30° C. and 130 rpm overnight, and cells necessary for fermentative production were prepared.

The inoculated cells were collected, the collected cells were inoculated into YPD liquid medium containing 10% glucose to a cell concentration of 0.5%, and stationary fermentation was carried out at 30° C. for 4 days. In this fermentation test, 2 types of production forms were tested. That is, production with the use of D-lactate prepared by adding 2.5% calcium carbonate (Nacalai Tesque Inc.) to a fermented mash and production with the use of free D-lactic acid without calcium carbonate were tested.

The fermented mash was collected 4 days after the initiation of fermentation, and the amounts of D-lactic acid and ethanol contained in the mash were measured using a multifunctional biosensor BF-4 (Oji Scientific Instruments). D-lactic acid was measured using the kit for measuring D-lactic acid (Oji Scientific Instruments) in accordance with the instructions included with the kit. The results are shown in FIG. 8 and FIG. 9.

Figure 8:
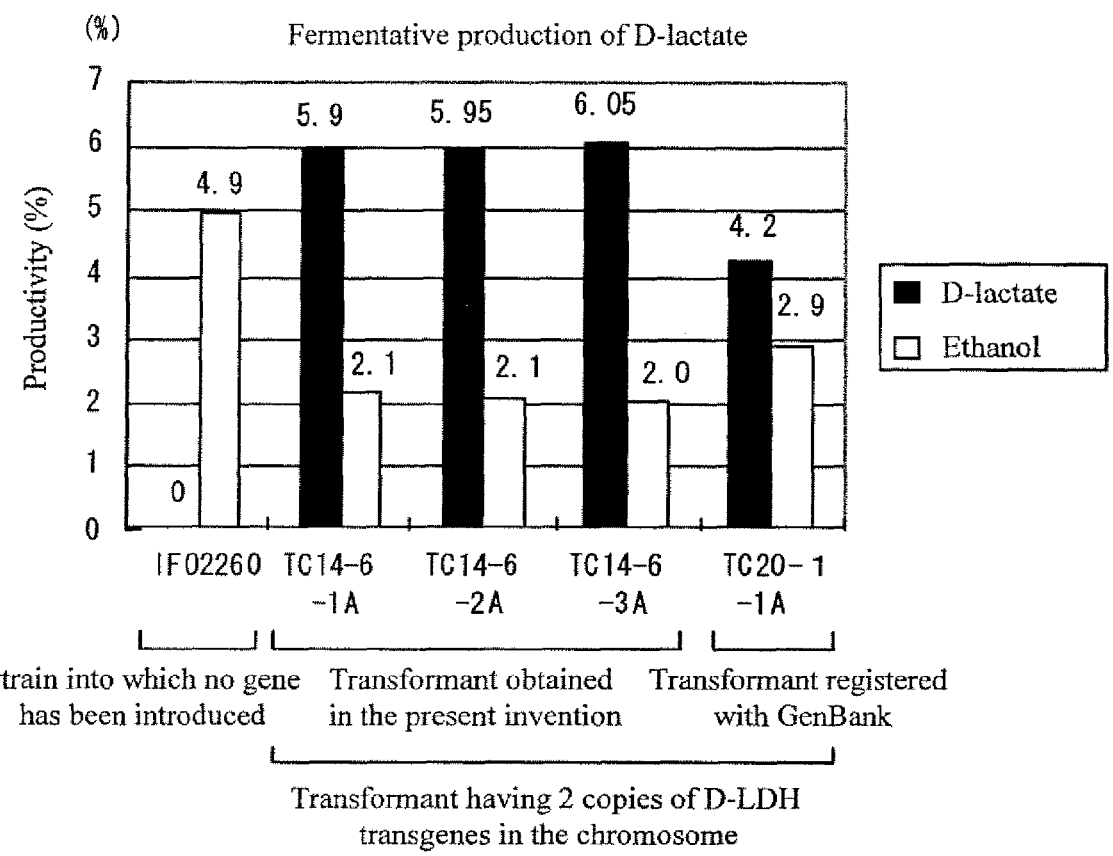
FIG. 8 is a graph showing the results of the fermentation test of D-lactate (calcium salt) produced by the parent strain and the transformant having chromosomally integrated transgenes, which shows the amount of D-lactate and ethanol produced by each strain.
Figure 9:
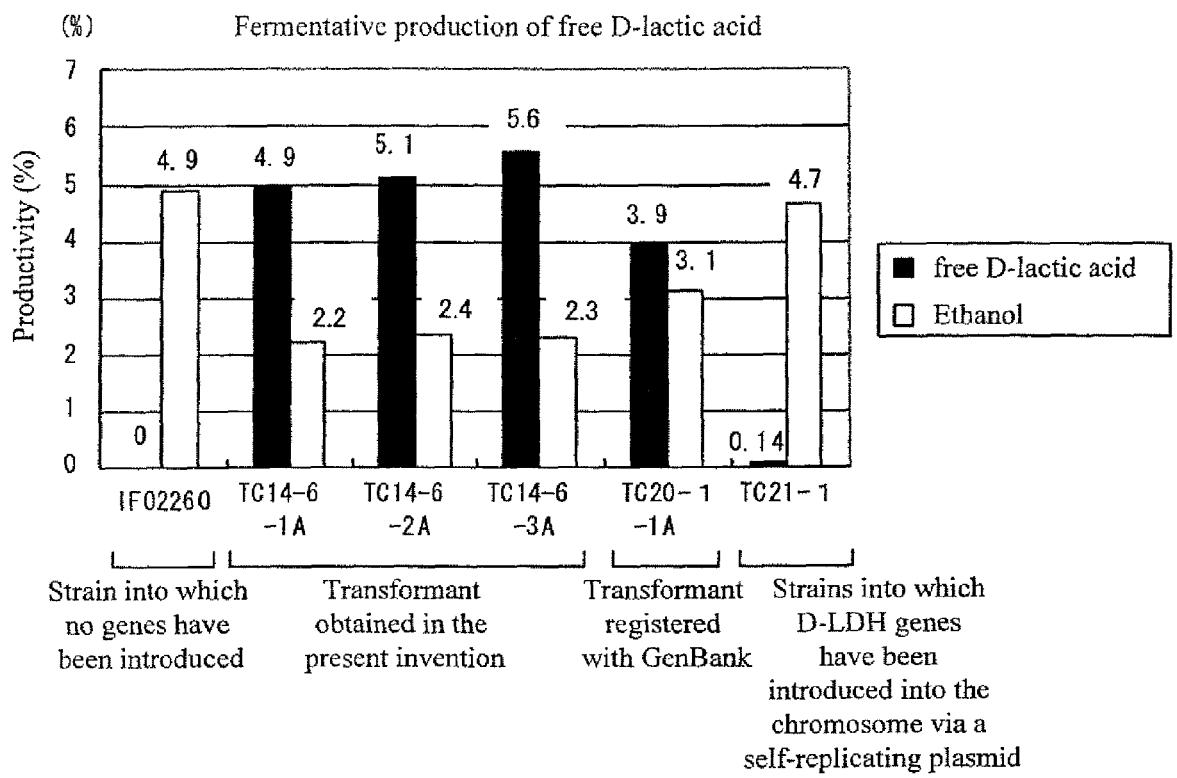
FIG. 9 is a graph showing the results of the fermentation test of free D-lactic acid produced by the parent strain, the transformant having chromosomally integrated transgenes, and the self-replicating plasmid transformant, which shows the amount of D-lactic acid and ethanol produced by each strain.

As shown in FIG. 8 and FIG. 9, the parent yeast strain (IFO2260) into which no genes had been introduced produced ethanol but did not produce D-lactic acid. In contrast, the 4 types of transformed yeast strains having chromosomally integrated transgenes prepared in Example 3 exhibited lower ethanol production than the parent strain but produced D-lactic acid.

Specifically, 4 types of strains, i.e., TC14-6-1A, TC14-6-2A, and TC14-6-3A, which are transformants into which D-LDHME genes had been introduced downstream of the PDC 1 promoter on the yeast chromosome, and TC20-1-1A into which the D-LDH genes had been introduced, produced D-lactic acid at concentrations of 4% to 6% and ethanol at concentrations of 2% to 3%. These transformants having chromosomally integrated transgenes did not produce L-lactic acid.

In contrast, the strains (TC21-1) into which D-LDHME genes had been introduced with the aid of self-replicating plasmids produced a very small amount of D-lactic acid. The amount of ethanol produced was the same as that of the strain IFO2260.

Accordingly, transformants having chromosomally integrated transgenes were found to be effective for D-LDH expression and D-lactic acid production. In particular, introduction of D-LDH genes (including D-LDHME genes) under the control of the PDC 1 promoters was found to be effective for the enhanced production of D-lactic acids.

Among the 4 aforementioned types of transformants having chromosomally integrated transgenes, 3 strains into which the D-LDHME genes had been incorporated downstream of the PDC1 promoters exhibited high D-lactic acid productivity of 5% or 6% but low ethanol productivity of 2%, i.e., the productivity of D-lactic acid was 2 or 3 times as high as that of ethanol. In the case of the transformant into which the D-LDH gene (GenBank Accession No. L29327) had been incorporated downstream of the PDC 1 promoter, D-lactic acid productivity was as low as approximately 4%, which was substantially the same as or approximately 1.3 times higher than ethanol productivity. Accordingly, D-LDHME genes were found to be effective for the enhanced production of D-lactic acid in transformants having chromosomally integrated transgenes.

The level of enhanced D-lactic acid production was approximately the same in the case of D-lactate (calcium) and in the case of free L-lactic acid.

Example 5

Gene Recombinant Yeast Strain Having Increased D-LDHME Copy Numbers

Among the D-lactic-acid-producing yeast strains prepared in Example 4, the strain TC14-6-3A was used to prepare a gene recombinant yeast strain having an increased copy number of the D-LDHME genes introduced. The D-LDHME genes were introduced into the strain TC14-6-3A in accordance with the method described in Example 3. Specifically, the D-LDHME genes were introduced into the strain TC14-6-3A in the same manner as in Example 3, except that the strain TC14-6-3A was used instead of the host yeast strain IFO2260.

The obtained strains into which genes had been introduced were designated as the strains TD-10-1B, TD1-10-3B, TD1-10-6A, and TD1-10-7D. The copy numbers of D-LDHME genes introduced in these 4 strains were inspected in the same manner as in Example 3. As a result, the copy number of the D-LDHME genes introduced was found to be 4.

Figure 10:
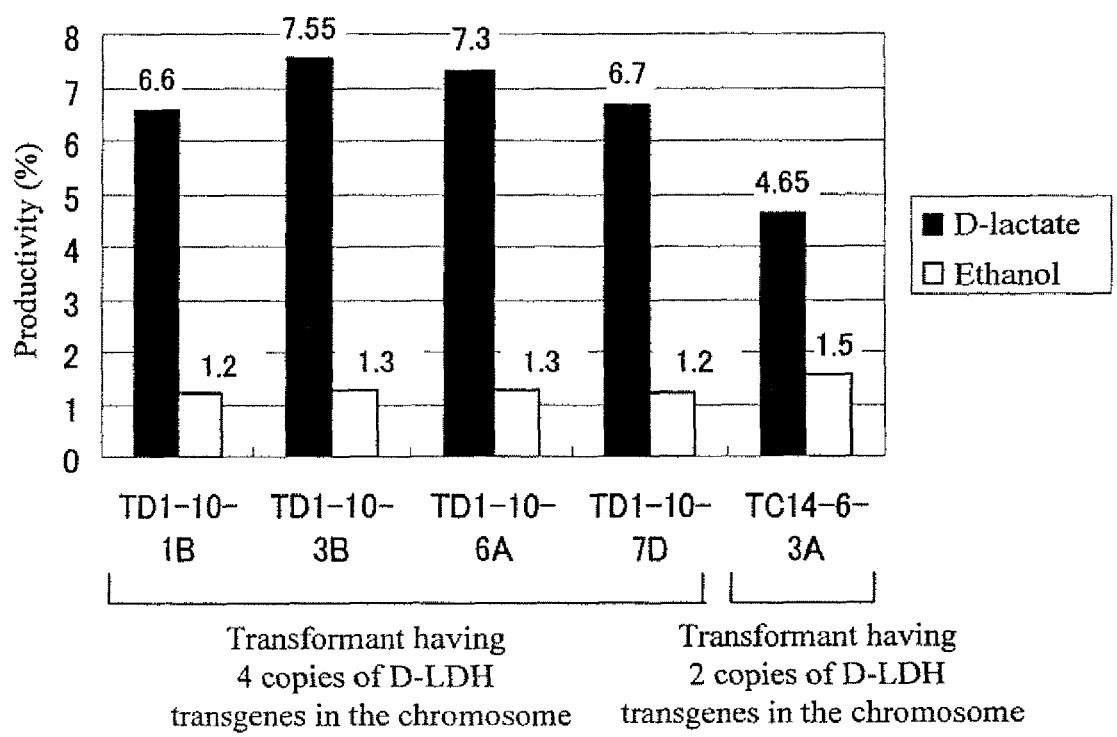
FIG. 10 is a graph showing the results of the fermentation test of free D-lactic acid produced by the strain into which 2 copies of the D-LDHME genes had been introduced and the strain into which 4 copies of the D-LDHME genes had been introduced, which shows the amount of D-lactic acid and ethanol produced by each strain.

Subsequently, these 4 types of strains were subjected to the fermentation test in accordance with the method described in Example 4 to inspect the amount of D-lactic acid produced. The results are shown in FIG. 10. As shown in FIG. 10, the amounts of D-lactic acids produced by the strains TD1-10-1B, TD1-10-3B, TD1-10-6A, and TD1-10-7D obtained in the present example were increased from the amount of D-lactic acid produced (4.65%) by the parent strain TC14-6-3A. All of the 4 strains obtained in the present example exhibited a decreased amount of ethanol production, compared to the parent strain.

This indicates that the capacity for D-lactic acid production of the transformed yeast strains could be improved by increasing the copy number of the D-LDHME genes introduced. In the present example, the transformed yeast strains into which 4 copies of D-LDHME genes had been introduced were examined. It should be noted that introduction of a larger copy number of D-LDHME genes can result in enhanced production of D-lactic acid. More specifically, the present example revealed that transformed yeast strains having superior capacity for D-lactic acid production can be prepared by increasing the copy number of the D-LDHME genes introduced.

All publications, patents, and patent applications cited herein are incorporated herein by reference in their entirety.

INDUSTRIAL APPLICABILITY

The present invention provides a technique for effectively producing D-lactic acid.

Sequence Listing Free Text

SEQ ID NOs: 6 to 11: artificial DNAs (primers)

---

What is claimed is:

1. An isolated or synthetic polynucleotide comprising a nucleotide sequence that encodes a protein having D-lactate dehydrogenase activity, wherein the protein comprises the amino acid sequence of SEQ ID NO: 4, except that the amino acid sequence has a substitution of amino acid 266 with Gly.

2. An isolated or synthetic polynucleotide comprising a nucleotide sequence that encodes a protein having D-lactate dehydrogenase activity, wherein the protein comprises the amino acid sequence of SEQ ID NO: 4, except that the amino acid sequence has a substitution of amino acid 266 with Gly and one or more of the following amino acid substitutions:
   amino acid 40 is substituted with Val;
   amino acid 112 is substituted with Ile;
   amino acid 131 is substituted with His;
   amino acid 139 is substituted with Ile;
   amino acid 181 is substituted with Glu;
   amino acid 267 is substituted with Leu;
   amino acid 268 is substituted with Phe;
   amino acid 269 is substituted with Asn;
   amino acid 270 is substituted with Glu;
   amino acid 271 is substituted with Asp;
   amino acid 272 is substituted with Trp;
   amino acid 273 is substituted with Ser;
   amino acid 274 is substituted with Gly;
   amino acid 276 is substituted with Glu;
   amino acid 277 is substituted with Phe;
   amino acid 287 is substituted with Ser;
   amino acid 292 is substituted with Leu; and
   amino acid 293 is substituted with Val.

3. The polynucleotide of claim 2, wherein the amino acid sequence has all of the following amino acid substitutions:
   amino acid 266 is substituted with Gly;
   amino acid 267 is substituted with Leu;
   amino acid 268 is substituted with Phe;
   amino acid 269 is substituted with Asn;
   amino acid 270 is substituted with Glu;
   amino acid 271 is substituted with Asp;
   amino acid 272 is substituted with Trp;
   amino acid 273 is substituted with Ser;
   amino acid 274 is substituted with Gly;
   amino acid 276 is substituted with Glu; and
   amino acid 277 is substituted with Phe.

4. The polynucleotide of claim 2, wherein the amino acid sequence comprises SEQ ID NO: 2.

5. A transformant comprising the polynucleotide of claim 1 or claim 2 in an expressible manner in a host.

6. A method for producing D-lactic acid comprising:
   culturing the transformant according to claim 5; and
   recovering at least one of D-lactic acid, a salt thereof, or a derivative thereof, from the culture product.

7. A method for producing a lactic acid polymer comprising:
   culturing the transformant according to claim 5;
   recovering at least one of D-lactic acid, a salt thereof, or a derivative thereof, from the culture product; and
   producing a lactic acid polymer using the recovered D-lactic acid or a derivative thereof as at least one polymerization material.

8. An isolated or synthetic polynucleotide comprising a nucleotide sequence that encodes a protein having D-lactate dehydrogenase activity, wherein the protein comprises an amino acid sequence that has at least 90% identity to SEQ ID NO:2 and has Gly at amino acid 266.

9. The polynucleotide of claim 8, wherein the amino acid sequence has at least 95% identity to SEQ ID NO: 2.

10. The polynucleotide of claim 8, wherein the amino acid sequence has:
    Gly at amino acid 266;
    Leu at amino acid 267;
    Phe at amino acid 268;
    Asn at amino acid 269;
    Glu at amino acid 270;
    Asp at amino acid 271;
    Trp at amino acid 272;
    Ser at amino acid 273;
    Gly at amino acid 274;
    Glu at amino acid 276; and
    Phe at amino acid 277.

11. The polynucleotide of claim 8, wherein the amino acid sequence consists of SEQ ID NO: 2.

12. A transformant comprising the polynucleotide of claim 8 in an expressible manner in a host.

13. A method for producing D-lactic acid comprising:
    culturing the transformant according to claim 12; and
    recovering at least one of D-lactic acid, a salt thereof, or a derivative thereof, from the culture product.

14. A method for producing a lactic acid polymer comprising:
    culturing the transformant according to claim 12;
    recovering at least one of D-lactic acid, a salt thereof, or a derivative thereof, from the culture product; and
    producing a lactic acid polymer using the recovered D-lactic acid or a derivative thereof as at least one polymerization material.

15. A DNA construct comprising the polynucleotide of any one of claims 1, 2, and 8 and a promoter.

* * * * *